(12) United States Patent
Abraham et al.

(10) Patent No.: US 10,668,059 B2
(45) Date of Patent: *Jun. 2, 2020

(54) COMPOSITIONS AND METHODS FOR THE PREVENTION AND TREATMENT OF MAST CELL-INDUCED VASCULAR LEAKAGE

(71) Applicant: Duke University, Durham, NC (US)

(72) Inventors: Soman N. Abraham, Chapel Hill, NC (US); Ashley L. St. John, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/648,119

(22) Filed: Jul. 12, 2017

(65) Prior Publication Data

US 2017/0368050 A1    Dec. 28, 2017

Related U.S. Application Data

(63) Continuation of application No. 14/388,140, filed as application No. PCT/US2013/032553 on Mar. 15, 2013, now Pat. No. 9,730,921.

(60) Provisional application No. 61/616,062, filed on Mar. 27, 2012.

(51) Int. Cl.

| | | |
|---|---|---|
| *A61K 31/47* | (2006.01) | |
| *A61K 31/352* | (2006.01) | |
| *A61K 31/4709* | (2006.01) | |
| *A61K 31/55* | (2006.01) | |
| *A61K 38/55* | (2006.01) | |
| *A61K 31/4535* | (2006.01) | |
| *G01N 33/573* | (2006.01) | |
| *G01N 33/68* | (2006.01) | |

(52) U.S. Cl.
CPC ............ *A61K 31/47* (2013.01); *A61K 31/352* (2013.01); *A61K 31/4535* (2013.01); *A61K 31/4709* (2013.01); *A61K 31/55* (2013.01); *A61K 38/55* (2013.01); *G01N 33/573* (2013.01); *G01N 33/6893* (2013.01); *G01N 2333/175* (2013.01); *G01N 2333/185* (2013.01); *G01N 2333/475* (2013.01); *G01N 2333/5412* (2013.01); *G01N 2333/96433* (2013.01); *G01N 2800/26* (2013.01); *G01N 2800/50* (2013.01); *Y02A 50/385* (2018.01); *Y02A 50/387* (2018.01); *Y02A 50/389* (2018.01); *Y02A 50/393* (2018.01); *Y02A 50/397* (2018.01)

(58) Field of Classification Search
CPC .. A61K 31/352; A61K 31/4535; A61K 31/47; A61K 31/4709; A61K 31/55; A61K 38/55; G01N 2333/175; G01N 2333/185; G01N 2333/475; G01N 2333/5412; G01N 2333/96433; G01N 2800/26; G01N 2800/50; G01N 33/573; G01N 33/6893
See application file for complete search history.

(56) References Cited

U.S. PATENT DOCUMENTS

| | | |
|---|---|---|
| 5,589,568 A | 12/1996 | Higashijima et al. |
| 6,849,714 B1 | 2/2005 | Bridon et al. |
| 6,887,470 B1 | 5/2005 | Bridon et al. |
| 7,256,253 B2 | 8/2007 | Bridon et al. |
| 9,301,999 B2 | 4/2016 | Staats et al. |
| 2002/0041898 A1 | 4/2002 | Unger et al. |
| 2005/0031630 A1 | 2/2005 | Pizzo et al. |
| 2006/0210551 A1 | 9/2006 | Lindsberg et al. |
| 2006/0276455 A1 | 12/2006 | Lindsberg et al. |
| 2008/0311138 A1 | 12/2008 | De Magistris |
| 2009/0053263 A1* | 2/2009 | Cunningham ......... A61K 35/55 424/204.1 |
| 2009/0176713 A1 | 7/2009 | Tymianski et al. |
| 2009/0227768 A1 | 9/2009 | Eisenberg et al. |
| 2011/0250130 A1 | 10/2011 | Benatuil et al. |
| 2015/0038530 A1 | 2/2015 | Abraham et al. |

FOREIGN PATENT DOCUMENTS

| | | |
|---|---|---|
| EP | 502718 | 9/1992 |
| WO | WO 9303749 | 3/1993 |
| WO | WO 2004/101737 | 11/2004 |
| WO | WO 2009/033719 | 3/2009 |
| WO | WO 2013/148366 | 10/2013 |

OTHER PUBLICATIONS

John W King, Medscape, 2018 (Year: 2018).*
CDC, Aug. 2015 (Year: 2015).*
Furuta et al, PLoS Neglected Tropical Diseases, vol. 6, Issue 21, Feb. 2012 (Year: 2012).*
Hu et al, Journal of Virology, p. 3347-3356, Jan. 11, 2012. (Year: 2012).*
Avirutnan et al, The Journal of Infectious Diseases, vol. 193, Issue 8, Apr. 15, 2006, pp. 1078-1088, (Year: 2006).*
Schoch, Ocul Immunol Inflamm. Feb. 2005;13(1):39-44 (Year: 2005).*
Kunder et al, The American Society of Hematology, 2011. (Year: 2011).*
Abraham, S.N. et al., "Mast cell-orchestrated immunity to pathogens," Nat. Rev. Immunol. (2010) 10(6):440-452.
Atrasheuskaya et al., "Anti-TNF antibody treatment reduces mortality in experimental dengue virus infection," FEMS Immunology and Medical Microbiology 35 (2003) 33-42.
Avirutnan et al., "Unmasking the role of mast cells in dengue," eLIFE, 2013, 3 pages.
Bois, P. et al., "Mast cells and histamine concentration in muscle and liver of dystrophic mice," (1964) Am. J. Physiol. 206:338-340.

(Continued)

*Primary Examiner* — Jean P Cornet
(74) *Attorney, Agent, or Firm* — Michael Best & Friedrich LLP

(57) ABSTRACT

Disclosed herein are methods of diagnosing and treating infectious disease characterized by a pathology that involves hemorrhaging or pathological vascular leakage.

13 Claims, 8 Drawing Sheets

(56) References Cited

OTHER PUBLICATIONS

Brett, J. et al., "Tumor Necrosis Factor/Cachectin Increases Permeability of Endothelial Cell Monolayers by a Mechanism Involving Regulatory G Proteins," (1989) J. Exp. Med. 169:1977-1991.

Brown et al., "A dominant role for Fc RII in antibody-enhanced dengue virus infection of human mast cells and associated CCL5 release," Journal of Leukocyte Biology, vol. 80, Dec. 2006, pp. 1242-1250.

Brown et al., "Dengue Virus Infection of Mast Cells Triggers Endothelial Cell Activation," Journal of Virology, Jan. 2011, p. 1145-1150.

Brown et al., "Dramatic caspase-dependent apoptosis in antibody-enhanced dengue virus infection of human mast cells," Journal of Leukocyte Biology, vol. 85, Jan. 2009, pp. 71-80.

Burlina, A.P. et al., "Mast cells contain large quantities of secretagogue-sensitive N-acetylaspartate," J. Neurochem. (1997) 69:1314-1317.

Busse, W.W. et al., "Leukotriene pathway inhibitors in asthma and chronic obstructive pulmonary disease," (1999) Clin. Exp. Allergy 29 Suppl 2:110-115.

Childs et al., "Effects of Hantaviral Infection on Survival, Growth and Fertility in Wild Rat (*Rattus nor vegicus*) Populations of Baltimore, Maryland," Journal of Wildlife Diseases, 25(4), 1989. pp. 469-476.

Dahlen, S.E. et al., "Leukotrienes promote plasma leakage and leukocyte adhesion in postcapillary venules: In vivo effects with relevance to the acute inflammatory response," (1981) Proc. Natl. Acad. Sci. USA 78:3887-3891).

De Filette et al. 'Recent progress in West Nile virus diagnosis and vaccination.' Veterinary Research 43:1-16, 2012.

Ferry, X. et al., "G protein-dependent activation of mast cell by peptides and basic secretagogues," Peptides (2002) 23:1507-1515.

Fink, J. et al., "Host Gene Expression Profiling of Dengue Virus Infection in Cell Lines and Patients," (2007) PLos Negl Trop Dis 1:e86.

Finkelman, F.D. et al., "Anaphylaxis: Lessons from mouse models," (2007) J. Allergy Clin. Immunol. 120:506-515.

Flower, R.J., "Inflammatory Effects of Prostaglandin D2 in Rat and Human Skin," (1976) Br. J. Pharmacol. 56:229-233).

Frangogiannis, N.G. et al., "Resident Cardiac Mast Cells Degranulate and Release Preformed TNF-a, Initiating the Cytokine Cascade in Experimental Canine Myocardial Ischemia/Reperfusion," (1998) Circulation 98:699-710.

Furuta et al., "Association of mast cell-derived VEGF and proteases in Dengue shock syndrom," PLoS: Neglected Tropical Diseases, vol. 6, Issue 2, Feb. 2012, (12 pages).

Grimbaldestron, M.A. et al., "Mast Cell-Deficient W-sash c-kit Mutant KitW-sh/W-sh Mice as a Model for Investigating Mast Cell Biology in Vivo," (2005) Am. J. Pathol. 167:835-848.

Guo, Y.B. et al., "Effect of mastoparan-1 on lipopolysaccharide-induced acute hepatic injury in mice," Zhonghua Shao Shang Za Zhi (2009) 25(1):53-56 Abstract only.

Gupta, B. et al., "Intracellular delivery of large molecules and small particles by cell-penetrating proteins and peptides," Adv. Drug Del. Rev. (2005) 57:637-651.

Halstead, "Dengue," Lancet (2007); 370: 1644-1652.

He, S. et al., "The induction of a prolonged increase in microvascular permeability by human mast cell chymase," (1998) Eur. J. Pharmacol. 352:91-98.

Hirata, Y. et al., "Identification of a 97-kDa mastoparan-binding protein involving in Ca2+ release from skeletal muscle sarcoplasmic reticulum," Mol. Pharmacol. (2000) 57:1235-1242.

Huang, C. et al., "The Tryptase, Mouse Mast Cell Protease 7, Exhibits Anticoagulant Activity in Vivo and in Vitro Due to Its Ability to Degrade Fibrinogen in the Presence of the Diverse Array of Protease Inhibitors in Plasma*," (1997) J. Biol. Chem. 272:31885-31893.

Kalesnikoff, J. et al., "New developments in mast cell biology," Nat. Immunol. (2008) 9(11):1215-1223.

King et al., "Dengue Virus Selectively Induces Human Mast Cell Chemokine Production," Journal of Virology, Aug. 2002, p. 8408-8419.

King et al., "Release of Vasoactive Cytokines by Antibody-Enhanced Dengue Virus Infection of a Human Mast Cell/Basophil Line," Journal of Virology, Aug. 2000, p. 7146-7150.

Koda, W. et al., "Evidence of the Participation of Peribiliary Mast Cells in Regulation of the Peribiliary Vascular Plexus Along the Intrahepatic Biliary Tree," (2000) Lab. Invest 80:1007-1017.

Koraka, P. et al., "Elevated Levels of Total and Dengue Virus-Specific Immunoglobulin E in Patients With Varying Disease Severity," (2003) J. Med. Viral. 70:91-98.

Kuby et al. 'Immunology.' Fourth Edition, Chapter 18: 449-465,2000.

Kunder, C.A. et al., "Mast cell modulation of the vascular and lymphatic endothelium," (2011) Blood 118:5383-5393.

Larsen, J.C., "U.S. Army botulinum neurotoxin (BoNT) medical therapeutics research program: past accomplishments and future directions," Drug Dev. Res. (2009) 70:266-278.

LeDuc, "Epidemiology of Hemorrhagic Fever Viruses," Reviews of Infectious Diseases. vol. II, Supplement, 4, May-Jun. 1989, S730-S735.

Leff, J.A. et al., "Montelukast, a Leukotriene-Receptor Antagonist, for the Treatment of Mild Asthma and Exercise-Induced Bronchoconstriction," (1998) N. Eng. J. Med. 339:147-152.

Lentschat, A. et al., "Mastoparan, a G protein agonist peptide, differentially modulates TLR4- and TLR2-mediated signaling in human endothelial cells and murine macrophages," J. Immunol. (2005) 174:4252-4261.

Low, J.G. et al., "Early Dengue Infection and Outcome Study (EDEN)—Study Design and Preliminary Findings," (2006) Ann Acad Med Singapore 35:783-789.

Mabalirajan, U. et al., "Short Report: TH2 Immune Response in Patients With Dengue During Defervescence: Preliminary Evidence," (2005) Am. J. Trop. Me d. Hyg. 72:783-785.

McClean, S.P. et al., "Refractory cholinergic urticaria successfully treated with ketotifen," (1989) J. Allergy Clin Immunol. 83:738-741.

McFadden, E.R. et al., "Medical Progress. Asthma," (1992) N. Engl. J. Med 327:1928-1937.

Mcgowen, A.L. et al., "The mast cell activator compound 48/80 is safe and effective when used as an adjuvant for intradermal immunization with Bacillus anthracis protective antigen," Vaccine (2009) 27(27):3544-3552.

Mclaughlan, J.B. et al., "Mast cell activators: a new class of highly effective vaccine adjuvants," Nature Med. (2008) 14(5):536-541.

Metzler et al. 'Solution structure of human CTLA-4 and delineation of a CD80/CD86 binding site conserved in CD28.' Nature Structural Bioi. 4:527-531,1997.

Ngo et al. 'Computational Complexity, Protein Structure Prediction, and the Levinthal Paradox'. The Protein Folding Problem and Tertiary Structure Prediction. Ed. K. Merz and S. LeGrand. Boston: Birkhauser, 1994, 491-495.

Oschatz, C. et al., "Mast Cells Increase Vascular Permeability by Heparin-Initiated Bradykinin Formation In Vivo," (2011) Immunity 34:258-268.

Pfeiffer et al., "The Petide Mastoparan Is a Potent Facilitator of the Mitochondrial Permeability Transition," J. Biol. Chem., 270:4923-4932, 1995.

Pulendran, B. et al., "A shot in the arm for mast cells," Nature Med. (2008) 14(5):489-490.

Raut, C. G. et al., "Susceptibility of Laboratory-Bred Rodents to the Experimental Infection With Dengue Virus Type," (1996) Acta. Virol. 40:143-146.

Sanchez, L.F. et al., "Degranulation and Histamine Release from Murine Mast Cells Sensitized with Dengue Virus-Immune Sera," (1986) Microbiol. Immunol 30:753-759.

Sendo, T. et al., "Involvement of proteinase-activated receptor-2 in mast cell tryptase-induced barrier dysfunction in bovine aortic endothelial cells," (2003) Cell Signal. 15:773-781.

Shelburne, C. et al., "Development of a novel anti-FimH vaccine using a mast cell activator as the adjuvant," J. Immunol. (2010) 184 Meeting Abstract Supplement 94:1.

(56) References Cited

OTHER PUBLICATIONS

Skolnick et al. 'From genes to protein structuree and function: novel applications of computational approaches in the genomic era.' Trends in Biotech 18:34-39, 2000.
St. John et al., "Immune surveillance by mast cells during dengue infection promotes natural killer (NK) and NKT-cell recruitment and viral clearance," PNAS Early Edition, 2011, 14 pages.
Suzanne et al., Dengue treatment and management, Medscape, 2015.
Theoharides, T.C. et al., "Antiallergic Drug Cromolyn May Inhibit Histamine Secretion by Regulating Phosphorylation of a Mast Cell Protein," (1980) Science 207:80-82.
Tseng C.S. et al., "Elevated levels of plasma VEGF inpatients with dengue hemorrhagic fever," (2005) FEMS Immunol. Med. Microbiol. 43:99-102.
Vitarana, T. et al., "Elevated tumour necrosis factor in dengue fever and dengue haemorrhagic fever," (1991) Ceylon Med. J. 36:63-65.
WebMd, Dengue Fever <http://www.webmd.com/a-to-z-guides/dengue-fever-reference> webpage accessed Sep. 16, 2016.
Williams,C.M. et al., "Mast Cells Can Amplify Airway Reactivity and Features of Chronic Inflammation in an Asthma Model in Mice," (2000)J. Exp. Med. 192:455-462.
World Health Organization et al., "Dengue, Guidelines for Diagnosis, Treatment, Prevention and Control," 2009, 4 pages.
Zellweger, R.M. et al., "Antibodies enhance infection of LSECs in a model of ADE-induced severe dengue disease," (2010) Cell Host Microbe. 7:128-139.
Zhang, P. et al., "A targeted therapeutic rescues botulinum toxin-A poisoned neurons," Nature (2008) 23 pages.
PCT/US2013/32553 International Search Report and Written Opinion dated May 29, 2013 (17 pages).
International Search Report and Written Opinion for Application No. PCT/US2010/50560 dated Mar. 28, 2011 (16 pages).
Australian Patent Office Examination Report for Application No. 2013240220 dated Dec. 20, 2016 (4 pages).
Singapore Patent Office Written Opinion for Application No. 11201406142X dated Aug. 7, 2016 (6 pages).
Singapore Patent Office Written Opinion for Application No. 11201406142X dated Dec. 29, 2015 (7 pages).
Singapore Patent Office Written Opinion for Application No. 11201406142X dated Jun. 16, 2015 (7 pages).
Singapore Patent Office Written Opinion for Application No. 11201406142X dated Mar. 6, 2017 (5 pages).
Thailand Patent Office Action for Application No. 1401005721 dated Nov. 11, 2015 (2 pages).
United States Patent Office Action for U.S. Appl. No. 13/498,258 dated Apr. 2, 2014 (9 pages).
United States Patent Office Action for U.S. Appl. No. 13/498,258 dated Oct. 7, 2013 (10 pages).
United States Patent Office Action for U.S. Appl. No. 13/498,258 dated Sep. 23, 2014 (9 pages).
United States Patent Office Final Office Action for U.S. Appl. No. 13/498,258 dated Jul. 20, 2015 (9 pages).
United States Patent Office Notice of Allowance for U.S. Appl. No. 13/498,258 dated Nov. 20, 2015 (7 pages).
United States Patent Office Action for U.S. Appl. No. 14/388,140 dated Jan. 29, 2016 (9 pages).
United States Patent Office Action for U.S. Appl. No. 14/388,140 dated Sep. 22, 2016 (14 pages).
United States Patent Office Notice of Allowance for U.S. Appl. No. 14/388,140 dated Apr. 12, 2017 (11 pages).
Mathur et al., "Breakdown of blood-brain barrier by virus-induced cytokine during Japanese encephalitis virus infection," Int. J. Exp. Pathol., 1992, 73(5):603-611.
India Intellectual Property Office Examination Report for Application No. 2323/KOLNP/2014 dated Feb. 14, 2019 (6 pages).

* cited by examiner

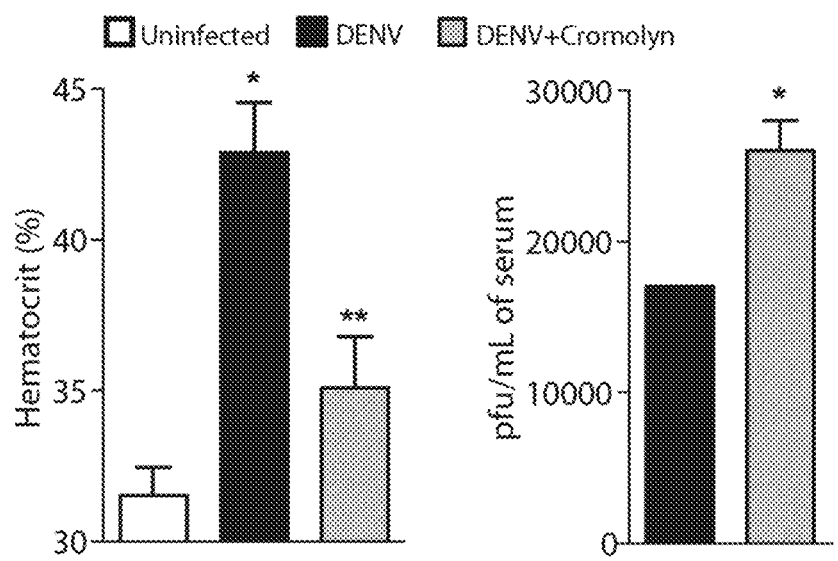
FIG. 6
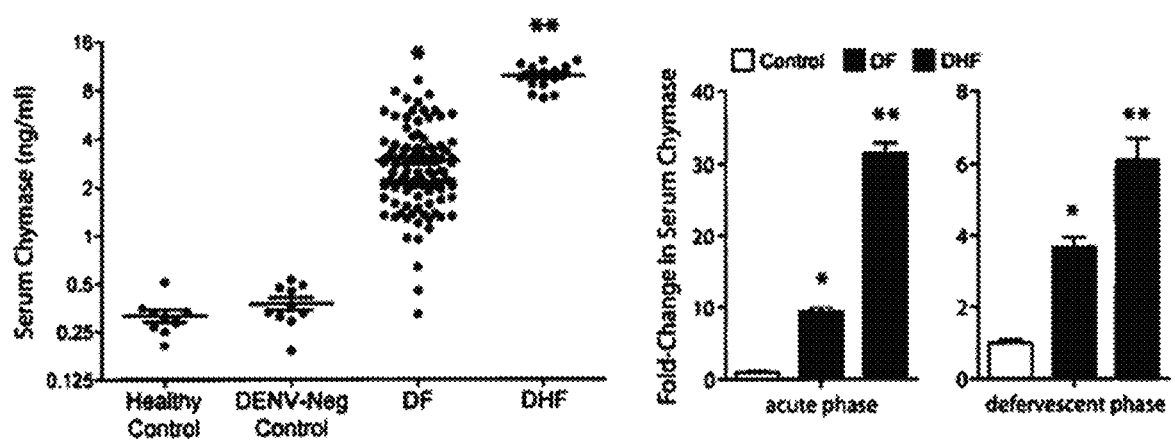
FIG. 7A
FIG. 7B

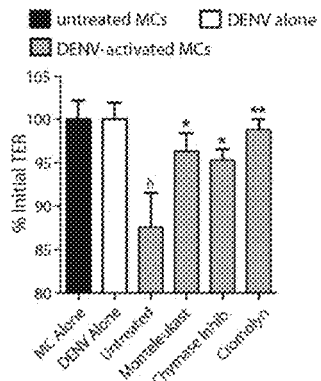
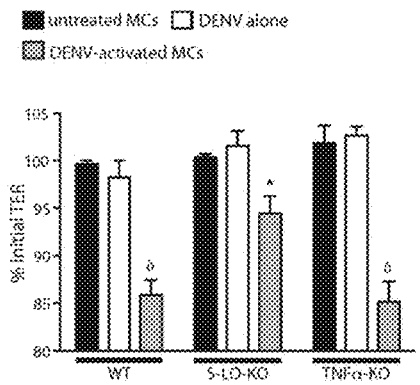
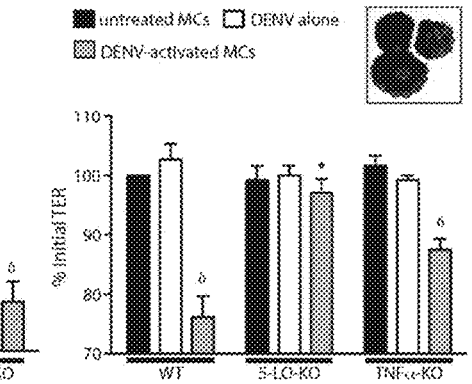
FIG. 8A  FIG. 8B
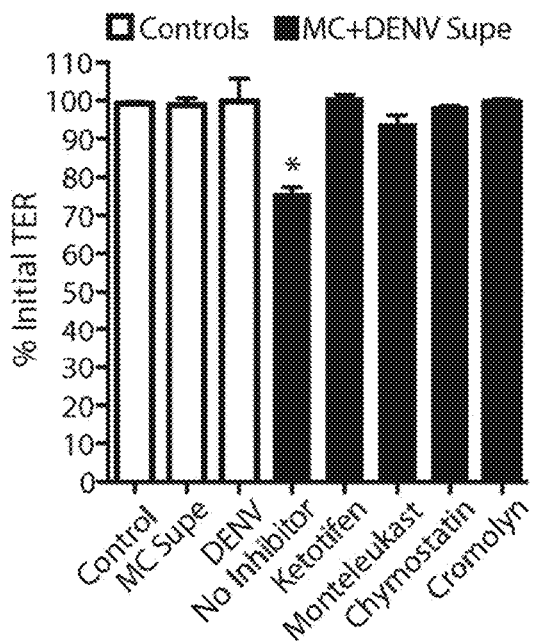
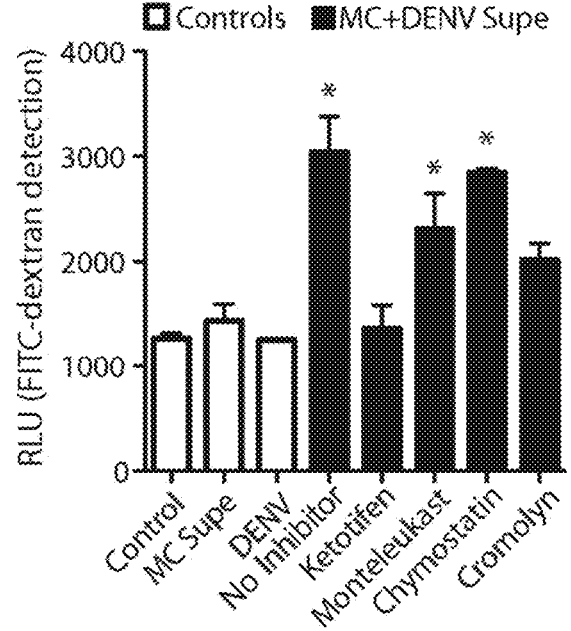
FIG. 9

Fig. 11A 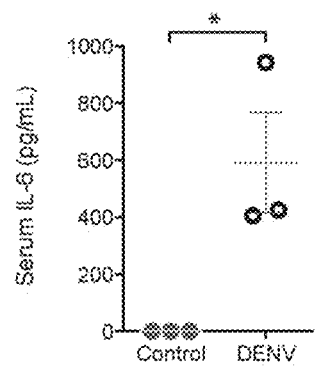 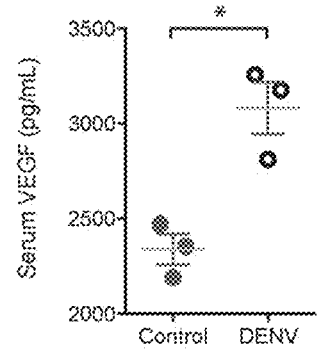 Fig. 11B
Fig. 11C 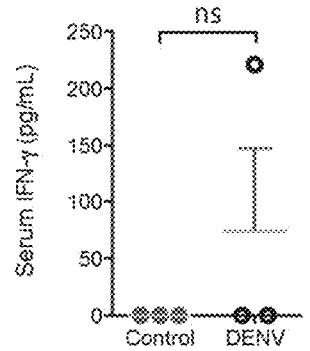 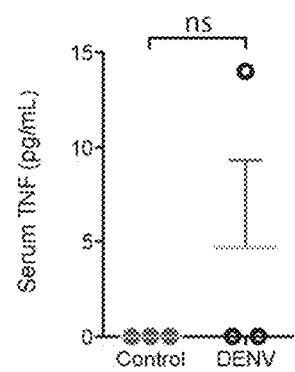 Fig. 11D
Fig. 11E 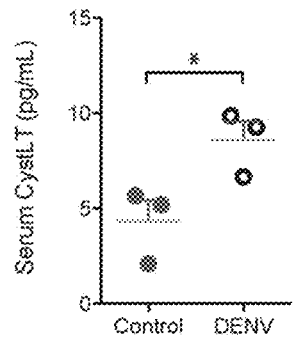 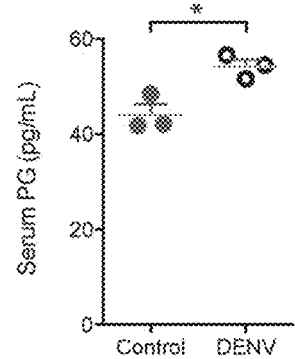 Fig. 11F

COMPOSITIONS AND METHODS FOR THE PREVENTION AND TREATMENT OF MAST CELL-INDUCED VASCULAR LEAKAGE

CROSS REFERENCE TO RELATED APPLICATIONS

This application is a continuation of U.S. patent application Ser. No. 14/388,140, filed Sep. 25, 2014, U.S. Patent No. 9,730,921, which is the U.S. national stage entry, under 35 U.S.C. § 371, of International Patent Application No. PCT/US2013/032553, filed Mar. 15, 2013, which claims priority to U.S. Provisional Patent Application No. 61/616,062, filed Mar. 27, 2012, the entire contents of each of which are hereby incorporated by reference.

STATEMENT OF GOVERNMENT INTEREST

This invention was made with government support under Grant Nos.: R21 DK077307, DK077159, and U01A1082107 awarded by NIH. The government has certain rights in the invention.

TECHNICAL FIELD

The disclosure relates to methods of treating infectious disease characterized by a pathology that involves hemorrhaging or pathological vascular leakage by administering a mast cell modulator. The disclosure also relates to methods of diagnosing and treating said infectious disease using mast cell-derived products as biomarkers.

BACKGROUND

A growing list of viral pathogens and emerging infectious diseases are characterized by a pathology in human that involves hemorrhaging or vascular leakage. These, including Ebola, Marburg, Hanta, West Nile, etc., are among the most deadly human pathogens and currently there are no approved treatments to prevent virus-induced bleeding in infected patients. As one example, millions of individuals are infected yearly with Dengue Virus (DENV), and some of these develop potentially deadly disease states, such as Dengue Hemorrhagic Fever (DHF) of Dengue Shock Syndrome (DSS), both of which involve increases in vascular permeability and hemorrhaging within internal organs. In severe cases, circulatory failure and death can occur. Currently, no targeted treatments exist to stabilize the vasculature during severe DENV complications, in part due to the current lack of understanding of the mechanisms of DENV-induced vascular leakage. Although the vascular leakage associated with DHF and DSS can result in death, a more common form of DENV infection is Dengue fever with limited morbidity. As there are currently no clinical tests to distinguish between the mild and more severe forms of DENV infections, in some settings, all patients are managed as if they have the severe form of the infection, which is unproductive and expensive, especially in endemic areas in the world. In other cases, individuals with DENV are not brought to the hospital or are released from the hospital, and do not have access to proper medical care when their disease becomes severe and life-threatening.

Mast cells (MC) are cellular regulators of vascular integrity, tone and function. They line blood vessels and produce many vasoactive mediators that have redundant functions in inducing vascular permeability. Some of these MC products are pre-stored and can act nearly instantaneously on vascular endothelium, including TNF, proteases (e.g., chymase and tryptase), and heparin. Other de novo synthesized vasoactive factors include leukotrienes, prostaglandins, VEGF, and TNF. With their activation, MC-derived factors act in concert to promote the breakdown of junctions between endothelial cells, leading to plasma leakage and edema within tissues, as well as to reduce clot formation and increase blood flow in the vicinity of MC-activated endothelium. Systemic or aberrant activation of MCs is a contributing factor to many pathological conditions associated with leakage of blood vessels, including anaphylaxis, asthma, aneurysm and others. Severe DENV outcomes in human patients have been epidemiologically associated with high levels of vasoactive factors that MCs produce, high levels of products that enhance MC responses, including IgE and MC-activation associated symptoms, such as rash and thrombocytopenia.

Several of the infectious diseases that are characterized by hemorrhaging in a subject have different disease states. Such states may be characterized as mild (i.e., exhibits non-life threatening symptoms) and severe (i.e., exhibit life-threatening symptoms). An example of this are those individuals who are infected with Dengue Virus (DENV), where some individuals exhibit non-life threatening symptoms such as fever, headache, muscle and/or joint pains, skin rash, etc. (i.e., mild) and other who progress to Dengue Hemorrhagic Fever (DHF) which includes life-threatening symptoms such as bleeding, low levels of blood platelets, and blood plasma leakage, or Dengue Shock Syndrome (DSS) which includes dangerously low blood pressure. Unfortunately, there currently are no clinical tests to distinguish between the mild and more severe forms of these kinds of infections. In addition, there are no targeted treatments to stabilize the vasculature during severe DENV infection. Furthermore, there are no clinical tests to distinguish between the mild and more severe forms of DENV infections. Accordingly, there is a need for compositions and methods for the prevention and treatment of MC-mediated vascular leakage in conditions such as DENV. Further, there exists a need for methods that can distinguish between mild and severe forms of infectious diseases, such as DENV.

SUMMARY

The present disclosure is directed to method of treating a subject having an infectious disease, wherein the infectious disease is characterized by a pathology that involves hemorrhaging or pathological vascular leakage in the subject, the method comprising administering to the subject a mast cell modulator. The mast cell modulator may stabilize mast cell activity in the subject. The mast cell modulator may comprise a mast cell stabilizer, wherein the mast cell stabilizer comprises a calcium channel blocker, a cytochrome P450 inhibitor or a histamine antagonist. The mast cell modulator may comprise at least one cromolyn, nedocromil, pemirolast, lodoxamide, tranilast, glucosamine, N-acetylglucosamine, FPL 52694, aloe vera, quercetin, chondroitin sulfate, dehydroleucodine, mast cell stabilizer TF002, rupatadine, loratadine, cetirizine, clemastime, fexofenadine, diphenhydramine, chlorpheniramine, azelastine, olopatadine, naphazoline, ketotifen, emedastine, and ebrotidine, combinations thereof and pharmaceutical compositions thereof. The mast cell modulator may inhibit mast cell-derived products in the subject. The mast cell modulator may comprise a leukotriene antagonist, a platelet activating factor inhibitor, a protease inhibitor, a VEGF inhibitor, a prostaglandin inhibitor, or a heparin inhibitor. The mast cell modulator may comprise at least one of zafirlukast, montelukast, pranlukast, zileuton, SM-12502, rupatadine, PAF-targeting antibodies, tumor necrosis factor immunomodulators, infliximab, adalimumab, certolizumab pegol, golimumab, etanercept, xanthine derivatives, methylxanthines like theophylline oxtriphylline, dyphylline, aminophylline, bupropion, curcumin, catechins, aprotinin, serpin, a chymase inhibitor, chymostatin, leupeptin, APC-336, SUN-C8257, NK3201, RO566852, BCEAB, NK3201, TEI-E548, APC-2095, RWJ-355871, bevacizumab, ranibizumab, lapatinib, sunitinib sorafenib, axitinib, pazopanib, thiazolidinediones, benzoxazole, benzthiazole, benzinidzole, CP105, 696, laropiprant, acetylsalicylic acid (ASA), indomethacin, sodium meclofenamate (FEN), phenylbutazone (PB), phloretin phosphates (PP), SC-19220, diethylcarbamazine citrate (DECC), protamine and polybrene, combinations thereof and pharmaceutical compositions thereof. The infectious disease is a viral hemorrhagic fever. The viral hemorrhagic fever is caused by a virus, wherein the virus is a member of at least one of the Arenaviridae, Filoviridae, Bunyaviridae, Flaviviridae, and Rhabdoviridae. The viral hemorrhagic fever is caused by at least one of Dengue Virus, Ebola virus, Marburg virus, Hanta virus, West Nile virus, St. Louis, Kunjin, Lassa Virus, Crimean-Congo hemorrhagic fever virus, Rift Valley fever virus, yellow fever, Japanese encephalitis virus, Lujo virus, Junin virus, Argentine hemorrhagic fever, Brazilian hemorrhagic fever, Bolivian hemorrhagic fever, argentine hemorrhagic fever, Garissa virus, SFTS virus, Hantan virus, omsk hemorrhagic fever virus, kyasanur forest disease virus, Langat virus, alkhurma virus, and Henipaviruses. The mast cell modulator may be administered at the onset of the infectious disease. The mast cell modulator may be administered after the onset of the infectious disease. The mast cell modulator may be administered prior to the onset of the infectious disease. The mast cell modulator may be administered prior to vascular leakage. The mast cell modulator may be administered after to vascular leakage.

The present disclosure is directed to a method of inhibiting or preventing hemorrhaging or vascular leakage induced by infectious disease in a subject, the method comprising administering to the subject a mast cell modulator. The mast cell modulator may stabilize mast cell activity in the subject. The mast cell modulator may comprise a mast cell stabilizer, wherein the mast cell stabilizer comprises a calcium channel blocker, a cytochrome P450 inhibitor or a histamine antagonist. The mast cell modulator may comprise at least one cromolyn, nedocromil, pemirolast, lodoxamide, tranilast, glucosamine, N-acetylglucosamine, FPL 52694, aloe vera, quercetin, chondroitin sulfate, dehydroleucodine, mast cell stabilizer TF002, rupatadine, loratadine, cetirizine, clemastime, fexofenadine, diphenhydramine, chlorpheniramine, azelastine, olopatadine, naphazoline, ketotifen, emedastine, and ebrotidine, combinations thereof and pharmaceutical compositions thereof. The mast cell modulator may inhibit mast cell-derived products in the subject. The mast cell modulator may comprise a leukotriene antagonist, a platelet activating factor inhibitor, a protease inhibitor, a VEGF inhibitor, a prostaglandin inhibitor, or a heparin inhibitor. The mast cell modulator may comprise at least one of zafirlukast, montelukast, pranlukast, zileuton, SM-12502, rupatadine, PAF-targeting antibodies, tumor necrosis factor immunomodulators, infliximab, adalimumab, certolizumab pegol, golimumab, etanercept, xanthine derivatives, methylxanthines like theophylline oxtriphylline, dyphylline, aminophylline, bupropion, curcumin, catechins, aprotinin, serpin, a chymase inhibitor, chymostatin, leupeptin, APC-336, SUN-C8257, NK3201, RO566852, BCEAB, NK3201, TEI-E548, APC-2095, RWJ-355871, bevacizumab, ranibizumab, lapatinib, sunitinib sorafenib, axitinib, pazopanib, thiazolidinediones, benzoxazole, benzthiazole, benzinidzole, CP105, 696, laropiprant, acetylsalicylic acid (ASA), indomethacin, sodium meclofenamate (FEN), phenylbutazone (PB), phloretin phosphates (PP), SC-19220, diethylcarbamazine citrate (DECC), protamine and polybrene, combinations thereof and pharmaceutical compositions thereof. The infectious disease is a viral hemorrhagic fever. The viral hemorrhagic fever is caused by a virus, wherein the virus is a member of at least one of the Arenaviridae, Filoviridae, Bunyaviridae, Flaviviridae, and Rhabdoviridae. The viral hemorrhagic fever is caused by at least one of Dengue Virus, Ebola virus, Marburg virus, Hanta virus, West Nile virus, St. Louis, Kunjin, Lassa Virus, Crimean-Congo hemorrhagic fever virus, Rift Valley fever virus, yellow fever, Japanese encephalitis virus, Lujo virus, Junin virus, Argentine hemorrhagic fever, Brazilian hemorrhagic fever, Bolivian hemorrhagic fever, argentine hemorrhagic fever, Garissa virus, SFTS virus, Hantan virus, omsk hemorrhagic fever virus, kyasanur forest disease virus, Langat virus, alkhurma virus, and Henipaviruses. The mast cell modulator may be administered at the onset of the infectious disease. The mast cell modulator may be administered after the onset of the infectious disease. The mast cell modulator may be administered prior to the onset of the infectious disease. The mast cell modulator may be administered prior to vascular leakage. The mast cell modulator may be administered after to vascular leakage.

The present disclosure is directed to a method of diagnosing and treating a subject having an infectious disease, wherein the infectious disease is characterized by a pathology that involves hemorrhaging or pathological vascular leakage in the subject, the method comprising: obtaining a biological sample from the subject; determining the level of at least one biomarker in the biological sample from the subject; comparing the level of the at least one biomarker in the biological sample to a reference level of the at least one biomarker; identifying the subject as having the infectious disease or having an increased risk of developing the infectious disease if the level of the at least one biomarker is greater than the reference level of the at least one biomarker; and administering an infectious disease treatment regimen to the subject identified as having the infectious disease or having an increased risk of developing the infectious disease. The infectious disease treatment regimen comprises a mast cell modulator. The reference level of the at least one biomarker is the level of the at least one biomarker in a control sample. The control sample is a sample from a healthy patient, a patient having the mild form of the infectious disease, or a patient having the severe form of the infectious disease. The reference level is about 0.18 ng/mL to about 0.5 ng/mL. The control sample is a sample from a patient having the mild form of the infectious disease. The reference level is about 0.8 ng/mL to about 6.0 ng/mL. The control sample is a sample from a patient having the severe form of the infectious disease. The reference level is greater than about 6.0 ng/mL. The level of the at least one biomarker in the biological sample is at least two times greater than the level of the at least one biomarker in the control sample, wherein the control sample is from a healthy patient. The mast cell modulator may stabilize mast cell activity in the subject. The mast cell modulator may comprise a mast cell stabilizer, wherein the mast cell stabilizer comprises a calcium channel blocker, a cytochrome P450 inhibitor or a histamine antagonist. The mast cell modulator may comprise at least one cromolyn, nedocromil, pemirolast, lodoxamide, tranilast, glucosamine, N-acetylglucosamine, FPL 52694, aloe vera, quercetin, chondroitin sulfate, dehydroleucodine, mast cell stabilizer TF002, rupatadine, loratadine, cetirizine, clemastime, fexofenadine, diphenhydramine, chlorpheniramine, azelastine, olopatadine, naphazoline, ketotifen, emedastine, and ebrotidine, combinations thereof and pharmaceutical compositions thereof. The mast cell modulator may inhibit mast cell-derived products in the subject. The mast cell modulator may comprise a leukotriene antagonist, a platelet activating factor inhibitor, a protease inhibitor, a VEGF inhibitor, a prostaglandin inhibitor, or a heparin inhibitor. The mast cell modulator may comprise at least one of zafirlukast, montelukast, pranlukast, zileuton, SM-12502, rupatadine, PAF-targeting antibodies, tumor necrosis factor immunomodulators, infliximab, adalimumab, certolizumab pegol, golimumab, etanercept, xanthine derivatives, methylxanthines like theophylline oxtriphylline, dyphylline, aminophylline, bupropion, curcumin, catechins, aprotinin, serpin, a chymase inhibitor, chymostatin, leupeptin, APC-336, SUN-C8257, NK3201, RO566852, BCEAB, NK3201, TEI-E548, APC-2095, RWJ-355871, bevacizumab, ranibizumab, lapatinib, sunitinib sorafenib, axitinib, pazopanib, thiazolidinediones, benzoxazole, benzthiazole, benzinidzole, CP105,696, laropiprant, acetylsalicylic acid (ASA), indomethacin, sodium meclofenamate (FEN), phenylbutazone (PB), phloretin phosphates (PP), SC-19220, diethylcarbamazine citrate (DECC), protamine and polybrene, combinations thereof and pharmaceutical compositions thereof. The infectious disease is a viral hemorrhagic fever. The viral hemorrhagic fever is caused by a virus, wherein the virus is a member of at least one of the Arenaviridae, Filoviridae, Bunyaviridae, Flaviviridae, and Rhabdoviridae. The viral hemorrhagic fever is caused by at least one of Dengue Virus, Ebola virus, Marburg virus, Hanta virus, West Nile virus, St. Louis, Kunjin, Lassa Virus, Crimean-Congo hemorrhagic fever virus, Rift Valley fever virus, yellow fever, Japanese encephalitis virus, Lujo virus, Junin virus, Argentine hemorrhagic fever, Brazilian hemorrhagic fever, Bolivian hemorrhagic fever, argentine hemorrhagic fever, Garissa virus, SFTS virus, Hantan virus, omsk hemorrhagic fever virus, kyasanur forest disease virus, Langat virus, alkhurma virus, and Henipaviruses. The mast cell modulator may be administered at the onset of the infectious disease. The mast cell modulator may be administered after the onset of the infectious disease. The mast cell modulator may be administered prior to the onset of the infectious disease. The mast cell modulator may be administered prior to vascular leakage. The mast cell modulator may be administered after to vascular leakage.

The present disclosure is directed to a method of diagnosing and treating a subject having a mild or severe form of an infectious disease, wherein the infectious disease is characterized by a pathology that involves hemorrhaging or pathological vascular leakage in the subject, the method comprising: obtaining a biological sample from the subject; determining the level of at least one biomarker in the biological sample from the subject; comparing the level of the at least one biomarker in the biological sample to a first reference level of the at least one biomarker and a second reference level of the at least one biomarker; correlating the level of the at least one biomarker in the biological sample with the mild or severe form of the infectious disease in the subject, where if the level of the at least one biomarker is greater than the first reference level of the at least one biomarker and the second reference level of the at least one biomarker, the subject is diagnosed as having the severe form of the infectious disease, and wherein if the level of the at least one biomarker is greater than the first reference level of the at least one biomarker but less than the second reference level of the at least one biomarker, the subject is diagnosed as having the mild form of the infectious disease; and administering an aggressive treatment regimen to the subject identified as having the severe form of the infectious disease or an infectious disease treatment regimen to the subject identified as having the mild form of the infectious disease. The infectious disease treatment regimen comprises a mast cell modulator. The first reference level of the at least one biomarker is the level of the at least one biomarker in a first control sample and the second reference level of the at least one biomarker is the level of the at least one biomarker in a second control sample. The first control sample is a sample from a healthy patient and the second control sample is a sample from a patient having the severe form of the infectious disease. The first reference level is about 0.18 ng/mL to about 0.5 ng/mL. The second reference level is greater than about 6.0 ng/mL. The aggressive treatment regimen comprises a mast cell modulator. The at least one biomarker comprises a mast cell-derived product. The mast cell-derived product comprises at least one of chymase, tryptase, leukotrienes, prostaglandins, tumor necrosis factor (TNF), vascular endothelial growth factor (VEGF), histamine, serotonin, carboxypeptidase A, β-hexosaminidase, metalloproteinases, endorphins, somatostatin (SRIF), kinins, urocortin, substance P, vasoactive intestinal peptide, granulocyte-macrophage colony-stimulating factor (GM-CSF), β-fibroblast growth factor, nerve growth factor, histones, chondroitin sulfate, heparin, hyaluronic acid, nitric oxide, angiotensin-1, heptatocyte growth factor, thrombin, stem cell factor, α2-macroglobulin, neurotensin, connective tissue-activating peptide III (CTAP-III), ApoA, ApoB, ApoE, porforin, granzymes, cathepsin, elastase, calreticulin, cathelicidins, serum trypsin inhibitors, chymotrypsin inhibitor, serpins, metabolic byproducts thereof, or combinations thereof. The biological sample of a subject is selected from the group consisting of tissue sample, bodily fluid, whole blood, plasma, serum, urine, bronchoalveolar lavage fluid, saliva, tissue biopsy, and a cell culture suspension or fraction thereof. The biological sample of a subject may be blood plasma or blood serum. The tissue sample comprises a somatic cell. The mast cell modulator may stabilize mast cell activity in the subject. The mast cell modulator may comprise a mast cell stabilizer, wherein the mast cell stabilizer comprises a calcium channel blocker, a cytochrome P450 inhibitor or a histamine antagonist. The mast cell modulator may comprise at least one cromolyn, nedocromil, pemirolast, lodoxamide, tranilast, glucosamine, N-acetylglucosamine, FPL 52694, aloe vera, quercetin, chondroitin sulfate, dehydroleucodine, mast cell stabilizer TF002, rupatadine, loratadine, cetirizine, clemastime, fexofenadine, diphenhydramine, chlorpheniramine, azelastine, olopatadine, naphazoline, ketotifen, emedastine, and ebrotidine, combinations thereof and pharmaceutical compositions thereof. The mast cell modulator may inhibit mast cell-derived products in the subject. The mast cell modulator may comprise a leukotriene antagonist, a platelet activating factor inhibitor, a protease inhibitor, a VEGF inhibitor, a prostaglandin inhibitor, or a heparin inhibitor. The mast cell modulator may comprise at least one of zafirlukast, montelukast, pranlukast, zileuton, SM-12502, rupatadine, PAF-targeting antibodies, tumor necrosis factor immunomodulators, infliximab, adalimumab, certolizumab pegol, golimumab, etanercept, xanthine derivatives, methylxanthines like theophylline oxtriphylline, dyphylline, aminophylline, bupropion, curcumin, catechins, aprotinin, serpin, a chymase inhibitor, chymostatin, leupeptin, APC-336, SUN-C8257, NK3201, RO566852, BCEAB, NK3201, TEI-E548, APC-2095, RWJ-355871, bevacizumab, ranibizumab, lapatinib, sunitinib sorafenib, axitinib, pazopanib, thiazolidinediones, benzoxazole, benzthiazole, benzinidzole, CP105, 696, laropiprant, acetylsalicylic acid (ASA), indomethacin, sodium meclofenamate (FEN), phenylbutazone (PB), phloretin phosphates (PP), SC-19220, diethylcarbamazine citrate (DECC), protamine and polybrene, combinations thereof and pharmaceutical compositions thereof. The infectious disease is a viral hemorrhagic fever. The viral hemorrhagic fever is caused by a virus, wherein the virus is a member of at least one of the Arenaviridae, Filoviridae, Bunyaviridae, Flaviviridae, and Rhabdoviridae. The viral hemorrhagic fever is caused by at least one of Dengue Virus, Ebola virus, Marburg virus, Hanta virus, West Nile virus, St. Louis, Kunjin, Lassa Virus, Crimean-Congo hemorrhagic fever virus, Rift Valley fever virus, yellow fever, Japanese encephalitis virus, Lujo virus, Junin virus, Argentine hemorrhagic fever, Brazilian hemorrhagic fever, Bolivian hemorrhagic fever, argentine hemorrhagic fever, Garissa virus, SFTS virus, Hantan virus, omsk hemorrhagic fever virus, kyasanur forest disease virus, Langat virus, alkhurma virus, and Henipaviruses. The mast cell modulator may be administered at the onset of the infectious disease. The mast cell modulator may be administered after the onset of the infectious disease. The mast cell modulator may be administered prior to the onset of the infectious disease. The mast cell modulator may be administered prior to vascular leakage. The mast cell modulator may be administered after to vascular leakage.

BRIEF DESCRIPTION OF THE DRAWINGS

FIG. 2A depicts the serum concentration of MCPT1 (a mast cell protease), which was quantified using serum obtained from WT or Sash mice, 24 and 48 hr after i.p. infection with $1 \times 10^6$ pfu DENV. MCPT1 was not detected (ND) in uninfected WT mice and uninfected or infected Sash mice. Error bars represent the SEM of ELISA replicates using pooled serum samples. To compare vascular leakage in infected vs. uninfected WT or Sash mice. FIG. 2B shows results of Evans blue quantitation in liver tissue. Images of mouse livers after perfusion are presented below the corresponding graph bars. FIG. 2C shows results of hematocrit analysis using blood obtained 24 hr after infection with DENV. For FIGS. 2B and 2C, error bars represent the SEM where values were obtained from individual infected mice n≥3. * indicates a significant increase over uninfected controls; p≤0.05.

FIG. 5A shows the results of Evans blue dye perfusion studies and hematocrit analysis performed to determine the vascular leakage in mice infected i.p. with $1 \times 10^6$ pfu of DENV. Serum was obtained from uninfected mice, DENV-infected and untreated mice, and mice that received MC-stabilizing or MC-product targeting treatments 24 hr after infection. Error bars represent the SEM of values obtained from individual animals n≥3. Data was analyzed by ANOVA with Bonferroni post-tests to determine significance. * indicates a significant increase over control (uninfected) values and ** indicates a significant decrease from DENV-infected, untreated values; p≤0.05. FIG. 5B shows the results of serum ELISA for MCPT1 was performed using pooled serum from DENV-infected, untreated mice and DENV-infected, cromolyn-treated mice. Significance was determined by ANOVA; δ indicates a significant decrease compared to untreated controls; p≤0.05.

FIG. 6 shows a graph indicating that cromolyn is effective in the IFN-α,β,γ-deficient mouse model to limit DENV-induced vasculopathy. Mice deficient in IFN-α,β,γ (strain AG129, which is frequently used as a DENV-permissive mouse strain) were infected with DENV by i.p. injection of $2 \times 10^6$ pfu of Eden2. After 1 day, treatment was initiated for some infected mice by administering i.p. injections of cromolyn (3 mg/mouse/day). On day 3, blood was collected from untreated and cromolyn-treated infected groups and uninfected controls. To generate the graph in the left panel, hematocrit analysis was performed using an automatic hematology analyzer to obtain values for blood from individual mice n≥3. Error bars represent the SEM and * indicates a significant increase over uninfected controls and ** indicates a significant decrease compared to DENV infection alone. The p-value for the comparison between uninfected vs. DENV-+cromolyn was not significant. The graph on the right panel depicts the plaque forming units obtained using pooled serum. Error bars represent the SEM of the assay, which was performed in replicates. Where no error bars are apparent, values obtained were the same for each replicate. * indicates a significant increase for the cromolyn-treated animals compared to infection alone.

FIGS. 7A and 7B show graphs indicating that DENV severity is linked to MC product chymase in humans. FIG. 7A shows a graph depicting the serum chymase concentration in human serum for healthy controls, DENV-negative febrile patients, and patients that were diagnosed with DF or DHF and positive for DENV by molecular tests. For DENV-Neg, DF and DHF patients, serum was collected during acute infection, 2-4 days after the onset of fever. Each dot represents the average concentration for an individual patent (n=10; 108 patients per group). FIG. 7B shows the data represented as fold-change in the serum concentration of chymase in patient samples obtained in the acute phase (left)

or defervescent phase (right graph; 4-7 days after fever onset). For both FIGS. 7A and 7B, ANOVA analysis was used to determine the significance of samples with Bonferroni's post-test to determine significance between groups. * indicates a significant increase over healthy controls and DENV-Neg control, and DF groups. p<0.0001.

FIGS. 8A and 8B show graphs indicating that MC products directly promote the permeability of vascular endothelial cells and that this permeability can be blocked with MC-targeting drugs.

FIG. 9 shows graphs indicating that Dengue-activated human mast cells promote permeability of human vascular endothelial cells in vitro and that this permeability can be blocked with MC-targeting drugs.

Figure 10:
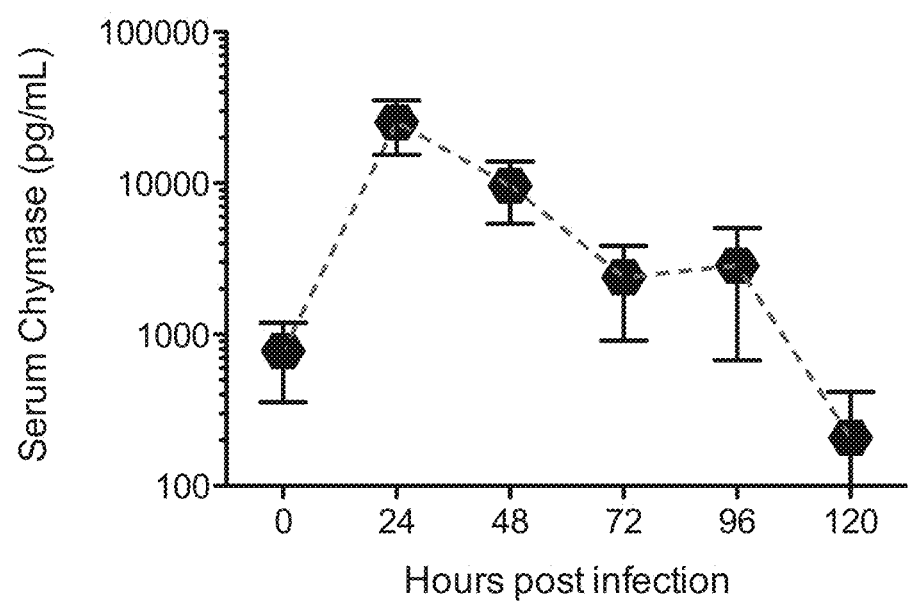

FIG. 10 shows a graph indicating the chymase levels in mice over a 5-day time course.

FIGS. 11A through 11F show graphs indicating the levels of IL-6, VEGF, IFN-γ, TNF, cysteinyl leukotrienes (CystLT) and prostaglandins (PG) in control and DENV infected mice.

DETAILED DESCRIPTION

The present disclosure relates to the prevention and treatment of infectious diseases characterized by a pathology that involves hemorrhaging or pathological vascular leakage in a patient by administering a mast cell modulator. These mast cell modulators may inhibit the activation of mast cells, i.e., inhibit degranulation and/or mast cell activity. The modulators may target and inhibit products released from mast cells upon activation of mast cells. These mast cell modulators may alternatively be stabilizers of mast cells, that is, these modulators stabilize the membranes of mast cells to prevent the release of histamine and related mediators.

The disclosure also relates to biomarkers for diagnosing and treating patients with said diseases. The biomarkers provide a means for distinguishing between mild and severe forms of said infectious disease. The treatments involve administering a mast cell modulator, as described above, to a patient in need thereof. The mast cell-derived products are used as biomarkers to identify individuals at highest risk for hemorrhagic complications.

The present disclosure is based on the present discovery that mast cells contribute to the leakiness of blood vessels during viral infection. As described herein, mast cells contribute to the promotion of virus-induced vascular permeability. Accordingly, the herein described drugs target mast cells or their products and ameliorate the vascular pathology that is characteristic of some viral infections. Because of this newly identified relationship between mast cells and viral-induced vascular permeability, the inventors have discovered that monitoring levels of mast cell products, such as chymase, in sera is effective to diagnose dengue infection, especially in those manifesting sever vascular leakage. For example, the disclosure describes how mast cell chymase was not only a potent biomarker of Dengue infection, but also surprisingly a predictor of its severity. Early detection of severe forms of Dengue allow for earlier administration of aggressive care to improve recovery rates.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used throughout the specification and the claims, the following terms have the following meanings:

The term "administration" or "administering," as used herein, refers to providing, contacting, and/or delivery of a mast cell modulator compound by any appropriate route to achieve the desired effect. These compounds may be administered to a subject in numerous ways including, but not limited to, orally, ocularly, nasally, intravenously, topically, as aerosols, suppository, etc. and may be used in combination.

The term "aggressive therapy" as used herein means a therapy that is designed to treat hemorrhaging and/or vascular leakage and, preferably, is effective to ameliorate at least one or more of the effects of the hemorrhaging and/or vascular leakage. Aggressive therapy may involve administering an agent (e.g., a drug) in an increased dosage or increased frequently than to a patient who is not a candidate for aggressive therapy, or selecting a therapy that is generally not given to a patient who is not a candidate for aggressive therapy.

The term "biomarker" as used herein refers to any quantifiable biological component that is unique to a particular physiological condition (e.g., an infectious disease). A biomarker may be a gene, an mRNA transcribed from said gene, or a protein translated from said mRNA. The gene may be a mast-cell-derived product. A measurable increase or decrease, of a biomarker level, relative to a control, such as an individual, group of individuals or populations, or alternatively, relative to subjects with varying degrees or types of infection (e.g., mild v. severe), may provide a diagnosis of a particular physiological condition.

The term "degranulation" as used herein refers to a cellular process that releases antimicrobial cytotoxic molecules from secretory vesicles called granules found inside some cells. In mast cells, degranulation may be induced when antigens interact with IgE molecules already bound to Fc receptors on the surface of mast cells resulting in the mast cell releasing a mixture of compounds including histamines, proteoglycans and serine proteases. Mast cells may also degranulate by direct injury or by activated complement proteins.

The term "Dengue fever" as used herein refers to a disease which is caused by the Dengue virus.

The term "Dengue Hemorrhagic fever" also known as Hemorrhagic dengue; Dengue shock syndrome; Philippine hemorrhagic fever; Thai hemorrhagic fever; Singapore hemorrhagic fever as used herein refers to a severe, potentially deadly infection caused by the Dengue virus The terms "Dengue virus" and "DENV" as used herein interchangeably refer to a virus that causes Dengue fever. It is a mosquito-borne single positive-stranded RNA virus of the family Flaviviridae. There are four serotypes of Dengue virus, which can all cause the full spectrum of Dengue fever.

The term "effective dosage" as used herein means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual.

The term "hemorrhaging" as used herein refers to a condition caused by an increase in vascular permeability wherein a discharge of blood occurs from blood vessels. Increased microvascular permeability may result in the pooling of fluid within organs thus causing damage and decreased blood volume which directly leads to shock. Alternatively, a copious discharge of blood may occur from blood vessel.

"Infectious disease" and "infectious disease characterized by a pathology that involves hemorrhaging" as used herein refers to any disease caused by an infectious agent (e.g., virus, bacteria, parasite, yeast, fungi and the like) that has, as one of its symptoms or side-effects, hemorrhaging/vascular leakage. Such infectious diseases include, but are not limited to, Ebola, Marburg, West Nile, Hanta, Dengue and the like.

"Mast cell" and "MC" as used herein refer to a resident cell of several types of tissues and contains many granules rich in histamine and heparin. Mast cells play a role in allergy and anaphylaxis and also a protective role as it is involved in wound healing and defense against pathogens.

"Mast cell activity" and "mast cell activation" as used herein refer to the release of mast cell-derived mediators from intracellular compartments of the mast cell and into the extracellular environment.

"Mast cell-derived product", "mast cell product" and "mast cell-derived mediators" as used herein interchangeably refer to products that are released into the extracellular environment when mast cells are activated. Mast cell products may be preformed mediators (from the granules), such as serine proteases, such as tryptase, histamine, serotonin, and proteoglycans, such as heparin, newly formed lipid mediators (eicosanoids), such as thromboxane, prostaglandin, leukotriene, platelet-activating factor, or cytokines, such as eosinophil chemotactic factor.

"Mast cell modulator" as used herein refers to those compounds that are capable of stabilizing a mast cell, or are capable of inhibiting mast cell-induced products The term "normal control" or "healthy control" as used herein means a sample or specimen taken from a subject, or an actual subject who does not have infectious disease, or is not at risk of developing infectious disease.

The term "pharmaceutically acceptable salt" as used herein refers to any pharmaceutically acceptable salt (e.g., acid or base) of a compound of the present invention which, upon administration to a subject, is capable of providing a compound of this invention or an active metabolite or residue thereof. "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "normal subject" as used herein means a healthy subject, i.e. a subject having no clinical signs or symptoms of infectious disease. The normal subject is clinically evaluated for otherwise undetected signs or symptoms of infectious disease, which evaluation may include routine physical examination and/or laboratory testing.

The term "predetermined cutoff" and "predetermined level" as used herein means an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). The disclosure provides exemplary predetermined levels. However, it is well-known that cutoff values may vary depending on the nature of the immunoassay (e.g., antibodies employed, reaction conditions, sample purity, etc.). It further is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

The term "reference activity level" or "reference" as used herein means an activity level of the biomarker in a sample group that serves as a reference against which to assess the activity level in an individual or sample group. For example, the reference activity level may be the activity of chymase in a control sample from stroke patients having occluded vessels that do not recanalize after the stroke patients are treated with a thrombolytic protease.

The term "risk assessment," "risk classification," "risk identification," or "risk stratification" as used herein interchangeably, means an evaluation of factors including biomarkers, to predict the risk of occurrence of future events including disease onset or disease progression, so that treatment decisions regarding the subject may be made on a more informed basis.

The term "sample," "test sample," "specimen," "biological sample," "sample from a subject," or "subject sample" as used herein interchangeably, means a sample or isolate of blood, tissue, urine, serum, plasma, amniotic fluid, cerebrospinal fluid, placental cells or tissue, endothelial cells, leukocytes, or monocytes, can be used directly as obtained from a subject or can be pre-treated, such as by filtration, distillation, extraction, concentration, centrifugation, inactivation of interfering components, addition of reagents, and the like, to modify the character of the sample in some manner as discussed herein or otherwise as is known in the art.

The term also means any biological material being tested for and/or suspected of containing an analyte of interest such as chymase. The sample may be any tissue sample taken or derived from the subject. In some embodiments, the sample from the subject may comprise protein. Any cell type, tissue, or bodily fluid may be utilized to obtain a sample. Such cell types, tissues, and fluid may include sections of tissues such as biopsy and autopsy samples, frozen sections taken for histological purposes, blood (such as whole blood), plasma, serum, sputum, stool, tears, mucus, saliva, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

Methods well-known in the art for collecting, handling and processing urine, blood, serum and plasma, and other body fluids, are used in the practice of the present disclosure. The test sample can comprise further moieties in addition to the analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples, a pre-processed archived sample, etc.), pretreatment of the sample is an option that can be performed for mere convenience (e.g., as part of a protocol on a commercial platform). The sample may be used directly as obtained from the subject or following pretreatment to modify a characteristic of the sample. Pretreatment may include extraction, concentration, inactivation of interfering components, and/or the addition of reagents.

The term "subject", "patient" or "subject in the method" as used herein interchangeably, means any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human. In some embodiments, the subject or subject may be a human or a non-human. In some embodiments, the subject may be a human subject at risk for developing or already having infectious disease.

"Therapeutically effective" as used herein refers to a dosage of a compound (e.g., a mast cell modulator) that is effective for eliciting a desired effect. This term as used herein may also refer to an amount effective at bringing about a desired in vivo effect in an animal, mammal, or human, such as reducing hemorrhaging, vascular leakage, inflammation, fever and the like. A therapeutically effective amount may be administered in one or more administrations (e.g., the compound may be given as a preventative treatment or therapeutically at any stage of disease progression, before or after vascular leakage symptoms, and the like), applications or dosages and is not intended to be limited to a particular formulation, combination or administration route. It is within the scope of the present disclosure that the mast cell modulator may be administered at various times during the course of infection of the subject. The times of administration and dosages used will depend on several factors, such as the goal of treatment (e.g., treating v. preventing), condition of the subject, etc. and can be readily determined by one skilled in the art.

The term "vascular leakage" and "pathological vascular leakage" as used herein interchangeably refer to an increase in vascular permeability, which is the capacity of a blood vessel wall to allow for the flow of small molecules (ions, water, nutrients) or even whole cells in and out of the vessel. The term "microvascular permeability" refers to the property of blood capillary walls that allows for the selective exchange of substances.

"Viral hemorrhagic fever" and "VHFs" as used herein refers to a group of illnesses that are caused by several distinct families of viruses. In general, the term "viral hemorrhagic fever" is used to describe a severe multisystem syndrome (multisystem in that multiple organ systems in the body are affected). Characteristically, the overall vascular system is damaged, and the body's ability to regulate itself is impaired. These symptoms are often accompanied by hemorrhage (bleeding) or plasma leakage from blood vessels; however, the bleeding itself rarely life-threatening. While some types of hemorrhagic fever viruses can cause relatively mild illnesses, many of these viruses cause severe, life-threatening disease.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. METHOD OF TREATING INFECTIOUS DISEASE INVOLVING HEMORRHAGING OR VASCULAR LEAKAGE

The present disclosure is directed to methods of treating infectious disease involving hemorrhaging or vascular leakage by using mast cell modulators. The mast cell modulators may be administered to a subject in need thereof. The mast cell modulator may be administered in an amount effective to treat the disease and/or inhibit or prevent hemorrhaging or vascular leakage. The present disclosure is also directed to methods of inhibiting or preventing hemorrhaging or vascular leakage induced by infectious disease by using mast cell modulators, as described herein.

3. MAST CELL MODULATORS

Mast cell modulators may include inhibitors of mast cell activities, which target specific mast cell products, or stabilizers of mast cell, which stabilize the mast cell membrane to prevent degranulation and/or release of histamines and other related mediators.

a. Inhibitors of Mast Cell Activities

Inhibitors of mast cell activities target specific mast cell products, i.e., products that are released from mast cell upon activation of mast cells or are involved in activating mast cells. During mast cell activation, granules or soluble factors (i.e., mast cell-derived products) are released from intracellular compartments into the extracellular environment. Inhibitors of mast cell activities may include leukotriene antagonists, platelet activating factor inhibitors, protease inhibitors, VEGF inhibitors, prostaglandins inhibitors and heparin inhibitors.

(1) Leukotriene Antagonists

Leukotrienes are a family of eicosanoid inflammatory mediators which are released by mast cells. Leukotriene antagonists, also referred to as leukasts, are drugs which inhibit and block the actions of leukotrienes. The two main approaches to blocking the actions of leukotrienes are inhibiting the synthetic pathway of leukotriene metabolism and blocking the leukotriene at its receptor, e.g., blocking the cysteinyl leukotriene at the CysLT1 receptor on target cells. Examples of leukotriene inhibitors include zafirlukast and montelukast (trade names Singulair, Montelo-10 and Monteflo), Pranlukast, and Zileuton.

(2) Platelet Activating Factor Inhibitors

Platelet activating factor, also known as PAF, PAF-acether or acetyl-glyceryl-ether-phosphorylcholine (AGEPC), are involved in activating mast cells, i.e., trigger degranulation of mast cells. PAF inhibitors block the activation of the mast cells and the chemotactic response. PAF inhibitors include SM-12502, rupatadine, PAF-targeting antibodies, tumor necrosis factor immunomodulators, such as infliximab, adalimumab, certolizumab pegol, golimumab, etanercept, xanthine derivatives, such as methylxanthines like theophylline (Theo-24, Uniphyl, Theo-Dur, Elixophyllin, Truxophyllin, Quibron-T, Quibron-T/SR, Theo-Time, TheoCap, Theochron, Theolair), oxtriphylline (Choledyl, Choledyl SA), dyphylline (Dilor, Dilor-400, Dylix, Lufyllin, Lufyllin-400, Neothylline), and aminophylline (Truphylline, Phyllocontin), bupropion, curcumin, and catechins.

(3) Proteases Inhibitors

Proteases, such as tryptases and chymases, are released by mast cells during degranulation. Protease inhibitors include aprotinin, serpin, chymase inhibitors, chymostatin, leupeptin, APC-336 (a biotinylated cysteine protease inhibitor related to K11777), SUN-C8257, NK3201, RO566852, BCEAB, NK3201, TEI-E548, APC-2095, and RWJ-355871.

(4) VEGF Inhibitors

VEGF, which stimulate vasculogenesis and angiogenesis, are released from mast cells. VEGF inhibitors include bevacizumab, ranibizumab, lapatinib, sunitinib sorafenib, axitinib, pazopanib, thiazolidinediones, benzoxazole, benzthiazole, benzinidzole, and CP105,696.

(5) Prostaglandins Inhibitors

Prostaglandins are involved in activating mast cells, i.e., trigger degranulation of mast cells. Prostaglandin inhibitors include Laropiprant, Acetylsalicylic acid (ASA), indomethacin, sodium meclofenamate (FEN), phenylbutazone (PB), phloretin phosphates (PP), SC-19220, and diethylcarbamazine citrate (DECC).

(6) Heparin Inhibitors

Heparin is an anticoagulant stored within the secretory granules of mast cells and released into the vasculature at sites of tissue injury. Heparin inhibitors include protamine and polybrene.

b. Mast Cell Stabilizers

Mast cell stabilizers may act by stabilizing the membranes of mast cells thus preventing the release of histamine and related mediators. Mast cell stabilizers, such as cromolyn may block calcium channels essential for mast cell degranulation as histamine vesicles cannot fuse to the cell membrane and degranulate without intracellular calcium. Mast cell stabilizers may also be inhibitors of particular cytochrome P450, such as rupatadine, or histamine antagonists, such as loratadine, cetirizine, clemastime, fexofenadine, diphenhydramine, chlorpheniramine, azelastine, olopatadine, naphazoline, ketotifen and its salt ketotifen fumarate (brand names Zaditor/Zaditen, Alaway, Zyrtec Itchy-Eye Drops, and Claritin Eye), emedastine, and ebrotidine.

4. METHODS OF USING BIOMARKERS FOR INFECTIOUS DISEASE THERAPY

The present invention is further directed to methods of using biomarkers for infectious disease therapy by quantifying the levels of at least one biomarker. The method includes quantifying at least one biomarker to determine the disease status of a patient. The biomarker is a mast cell-derived product, or degradation or metabolic breakdown product thereof, and include chymase, tryptase, leukotrienes, prostaglandins, tumor necrosis factor (TNF), vascular endothelial growth factor (VEGF), histamine, serotonin, carboxypeptidase A, β-hexosaminidase, metalloproteinases, such as MMP-1,2,7,9,10, endorphins, somatostatin (SRIF), kinins, urocortin, substance P, vasoactive intestinal peptide, granulocyte-macrophage colony-stimulating factor (GM-CSF), β-fibroblast growth factor, nerve growth factor, histones, chondroitin sulfate, heparin, hyaluronic acid, nitric oxide, angiotensin-1, heptatocyte growth factor, thrombin, stem cell factor, α2-macroglobulin, neurotensin, connective tissue-activating peptide III (CTAP-III), ApoA, ApoB, ApoE, porforin, granzymes, cathepsin, elastase, calreticulin, cathelicidins, serum trypsin inhibitors, chymotrypsin inhibitor, serpins, or combinations thereof.

a. Chymase

Chymases are a family of serine proteases found primarily in mast cells. They show broad peptidolytic activity and are involved in a variety of functions. Chymases also convert angiotensin I to angiotensin II and thus play a role in hypertension and atherosclerosis.

b. IL-6

Interleukins are a group of cytokines that are secreted proteins and signaling molecules. Interleukin 6 (IL6), also known as B-cell stimulatory factor-2 (BSF-2) and interferon beta-2, is a cytokine involved in a wide variety of biological functions. It plays an essential role in the final differentiation of B-cells into IG-secreting cells, as well as inducing myeloma/plasmacytoma growth, nerve cell differentiation and acute-phase reactants.

c. VEGF

VEGF is a signal protein produced by cells that stimulates vasculogenesis and angiogenesis.

d. Cysteinyl Leukotrienes (CystLT)

Cysteinyl leukotrienes are a family of inflammatory lip mediators synthesized from arachidonic acid. Cysteinyl leukotrienes make up the slow-reacting substance of anaphylaxis (SRS-A).

e. Prostaglandins (PG)

A prostaglandin is any member of a group of lipid compounds that are derived enzymatically from fatty acids and have important functions in the animal body.

5. METHOD FOR IDENTIFYING AND TREATING A SUBJECT SUFFERING FROM INFECTIOUS DISEASE

The present disclosure is directed to a method for identifying and treating a subject suffering from infectious disease by quantifying the level of at least one biomarker. The method includes the steps of obtaining a biological sample from a subject, determining the level of at least one biomarker in the biological sample from the subject; comparing the level of the at least one biomarker in the biological sample to a reference level of the at least one biomarker; identifying the subject as having the infectious disease or having an increased risk of developing the infectious disease if the level of the at least one biomarker is greater than the reference level of the at least one biomarker; and administering an infectious disease treatment regimen to the subject identified as having the infectious disease or having an increased risk of developing the infectious disease.

6. METHODS OF DISTINGUISHING SEVERE FORM OF THE INFECTIOUS DISEASE

The present disclosure is directed to a method for distinguishing a subject suffering from a severe form of the infectious disease from a subject suffering from a mild form of the infectious disease or is normal by quantifying the level of at least one biomarker. The method includes the steps of obtaining a biological sample from the subject; determining the level of at least one biomarker in the biological sample from the subject; comparing the level of the at least one biomarker in the biological sample to a first reference level of the at least one biomarker and a second reference level of the at least one biomarker; correlating the level of the at least one biomarker in the biological sample with the mild or severe form of the infectious disease in the subject, wherein if the level of the at least one biomarker is greater than the first reference level of the at least one biomarker and the second reference level of the at least one biomarker, the subject is diagnosed as having the severe form of the infectious disease, and wherein if the level of the at least one biomarker is greater than the first reference level of the at least one biomarker but less than the second reference level of the at least one biomarker, the subject is diagnosed as having the mild form of the infectious disease; and administering an aggressive treatment regimen to the subject identified as having the severe form of the infectious disease or an infectious disease treatment regimen to the subject identified as having the mild form of the infectious disease.

a. Dengue Fever

Dengue fever is a disease caused by the Dengue virus. Dengue virus is a small single-stranded RNA virus comprising four distinct serotypes (DEN-1 to -4).

(1) Mild Form

The mild form of Dengue fever, probable Dengue, may be determined using the following criteria: live in/travel to dengue endemic area; fever and two of the following criteria: nausea, vomiting, rash, aches and pains, Tourniquet test positive, leukopenia, and any warning sign. A warning sign includes abdominal pain or tenderness, persistent vomiting, clinical fluid accumulation, mucosal bleed, lethargy, restlessness, liver enlargement >2 cm, and a laboratory test of an increase in hematocrit concurrent with rapid decrease in platelet count. Dengue may also be determined by a laboratory test.

(2) Severe Form

The severe form of Dengue may be characterized as severe plasma leakage, which lead to shock and fluid accumulation with respiratory distress, severe bleeding, and severe organ involvement (for example, Liver: AST or ALT greater than 1000, CNS: impaired consciousness, and heart and other organs).

7. METHODS OF DIAGNOSING, PROGNOSTICATING, AND/OR STRATIFYING RISK OF INFECTIOUS DISEASE USING A COMBINATION OF MARKERS

The present disclosure is directed to a method of diagnosing, prognosticating, and/or stratifying risk of infectious disease by quantifying the levels of at least two or more biomarkers. The method includes the steps of obtaining a biological sample from a subject, determining the levels of a first biomarker and a second biomarker in the biological sample from the subject; comparing the levels of the first biomarker and the second biomarker in the biological sample to reference levels of the first biomarker and the second biomarker; diagnosing the subject as having the infectious disease or having an increased risk of developing the infectious disease if the level of the first biomarker is greater than the reference level of the first biomarker and the level of the second biomarker is greater than the reference level of the second biomarker; and administering an infectious disease treatment regimen to the subject diagnosed as having the infectious disease or having an increased risk of developing the infectious disease.

8. METHODS FOR PROVIDING A DIAGNOSIS OF A SUBJECT HAVING INFECTIOUS DISEASE

The present disclosure is directed to a method for providing a diagnosis of a subject having infectious disease by quantifying the level of at least one biomarker. The method includes the steps of obtaining a biological sample from a subject, determining the level of at least one biomarker in the biological sample from the subject; comparing the level of the at least one biomarker in the biological sample to a reference level of the at least one biomarker; diagnosing the subject as having the infectious disease or having an increased risk of developing the infectious disease if the level of the at least one biomarker is greater than the reference level of the at least one biomarker. The method may further include administering an infectious disease treatment regimen to the subject diagnosed as having the infectious disease or having an increased risk of developing the infectious disease.

9. METHODS FOR DETERMINING THE RISK OF A SUBJECT OF DEVELOPING INFECTIOUS DISEASE

The present disclosure is directed to a method for determining the risk of a subject of developing an infectious disease by quantifying the level of at least one biomarker. The method includes the steps of obtaining a biological sample from a subject, determining the level of at least one biomarker in the biological sample from the subject; comparing the level of the at least one biomarker in the biological sample to a reference level of the at least one biomarker; determining the subject as having an increased risk of developing the infectious disease if the level of the at least one biomarker is greater than the reference level of the at least one biomarker. The method may further include administering an infectious disease treatment regimen to the subject identified as having an increased risk of developing the infectious disease.

10. METHODS OF MONITORING THE PROGRESSION OF INFECTIOUS DISEASE

The present disclosure is directed to a method of monitoring the progression of infectious disease in a subject by quantifying the level of at least one biomarker. The method includes the steps of obtaining a biological sample from a subject, determining the level of at least one biomarker in the biological sample from the subject; correlating the level of the at least one biomarker in the biological sample with the progression of infectious disease in the subject, wherein if the level of the at least one biomarker is higher as compared to the level of the biological marker in an earlier biological sample from the subject, the subject is identified as having progression of infectious disease. The method may further include administering an aggressive treatment regimen to the subject identified as having progression of infectious disease.

11. METHOD FOR DETERMINING IF A SUBJECT IS RESPONDING TO THE ADMINISTRATION OF A PHARMACEUTICAL COMPOSITION

The present disclosure is directed to a method for determining if a subject is responding to the administration of one or more pharmaceutical compositions by quantifying the level of the at least one biomarker. The method optionally comprises an assay as described herein, where the level of the at least one biomarker is assessed before and following treatment of the subject with one or more pharmaceutical compositions or where the level of the at least one biomarker is assessed following such treatment and the level of the at least one biomarker is compared against a predetermined level. An unfavorable level of the at least one biomarker observed following treatment confirms that the subject will not benefit from receiving further or continued treatment, whereas a favorable concentration or amount of the at least one biomarker following treatment confirms that the subject will benefit from receiving further or continued treatment. This confirmation assists with management of clinical studies, and provision of improved patient care.

The method includes the steps of obtaining a biological sample from a subject, determining the level of the at least one biomarker in the biological sample from the subject; comparing the level of the at least one biomarker in the biological sample to a reference level of the at least one biomarker, wherein an altered level of the at least one biomarker indicates that the subject is not responding to the administration of one or more pharmaceutical compositions, and adjusting the treatment of the subject if the subject is not responding to the administration of one or more pharmaceutical compositions.

12. INFECTIOUS DISEASES

The methods described above are directed to treating infectious disease having a hemorrhage or vascular leakage in a subject. The subject to be treated or diagnosed by the methods described above may be a subject or patient suffering from infections disease, which is characterized by a pathology that involves hemorrhaging or pathological vascular leakage by increasing vascular permeability. An infectious disease characterized by a pathology that involves hemorrhaging or pathological vascular leakage by increasing vascular permeability may be caused by viruses or bacteria.

a. Viral Hemorrhagic Fever

The subject may be suffering from a viral hemorrhagic fever. The virus may be a virus known to cause hemorrhagic fevers, such as RNA viruses of the families Arenaviridae, Filoviridae, Bunyaviridae, Flaviviridae, and Rhabdoviridae. The Arenaviridae family includes the viruses responsible for Lassa fever, Lujo virus, Argentine, Bolivian, Brazilian and Venezuelan hemorrhagic fevers. The Bunyaviridae family includes the members of the Hantavirus genus that cause hemorrhagic fever with renal syndrome (HFRS), the Crimean-Congo hemorrhagic fever (CCHF) virus from the Nairovirus genus, Garissa virus from the Orthobunyavirus and the Rift Valley fever (RVF) virus from the Phlebovirus genus. The Filoviridae family includes Ebola virus and Marburg virus. The Flaviviridae family includes Dengue, yellow fever, and two viruses in the tick-borne encephalitis group that cause VHF: Omsk hemorrhagic fever virus and Kyasanur Forest disease virus. The Rhabdoviridae family includes rabies.

Examples of such viruses include Dengue Virus, Ebola virus, Marburg virus, Hanta virus, West Nile virus (including St. Louis and Kunjin), Lassa Virus, Crimean-Congo hemorrhagic fever virus, Rift Valley fever virus, yellow fever, Japanese encephalitis virus, Lujo virus, Junin virus, Argentine hemorrhagic fever, Brazilian hemorrhagic fever, Bolivian hemorrhagic fever, argentine hemorrhagic fever, Garissa virus, SFTS virus, Hantan virus, omsk hemorrhagic fever, virus, kyasanur forest disease virus, Langat virus, alkhurma virus, and Henipaviruses (e.g., Hendra virus, Nipah virus and Cedar virus).

b. Control

The method for distinguishing a subject suffering from an infectious disease characterized by a pathology that involves hemorrhaging or pathological vascular leakage is accomplished by quantifying the levels of at least one biomarker. It may be desirable to include a control in any of the herein described methods. The control may be a biological sample. Standard curves may be provided, with which assay results for the biological sample may be compared. Such standard curves present levels of marker as a function of assay units, i.e. luminescent signal intensity. Using samples taken from multiple donors, standard curves can be provided for control levels of one or more biomarkers in normal tissue, as well as for "at-risk" levels of the biomarker(s) in tissue taken from donors. The sample may be from a healthy subject, a subject having a mild form of the disease, or a subject having a severe form of the disease. The control sample may correspond to levels of one or more biomarkers from subjects grouped on the basis of any type of infection, ethnicity, geography, etc.

Any cell type, tissue, or bodily fluid may be utilized as the sample. Such cell types, tissues, and fluid may include sections of tissues such as biopsy and autopsy samples, frozen sections taken for histologic purposes, blood, plasma, serum, sputum, stool, tears, mucus, saliva, hair, and skin. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose. Archival tissues, such as those having treatment or outcome history, may also be used. The control may be a reference level of a biomarker.

(1) Healthy Subjects

The reference level in this methods described above can be the level of chymase in a healthy patient. Levels less than or equal to about 1.0 ng/mL, about 0.9 ng/mL, about 0.8 ng/mL, about 0.7 ng/mL, about 0.6 ng/mL, about 0.5 ng/mL, about 0.4 ng/mL, about 0.3 ng/mL, about 0.2 ng/mL, about 0.1 ng/mL, or about 0.05 ng/mL of chymase in serum identify the subject as being healthy.

(2) Infectious Disease

The reference level in this method described above can be the level of chymase in a healthy patient. Levels greater than or equal to about 0.05 ng/mL, about 0.1 ng/mL, about 0.2 ng/mL, about 0.3 ng/mL, about 0.4 ng/mL, about 0.5 ng/mL, about 0.6 ng/mL, about 0.7 ng/mL, about 0.8 ng/mL, about 0.9 ng/mL, or about 1.0 ng/mL, of chymase in serum identify the subject as having or at risk of having infectious disease associated with hemorrhaging and vascular leakage.

The reference level in this method can be the level of chymase in a patient with a mild form of infectious disease. Levels greater than or equal to about 0.5 ng/mL, about 0.6 ng/mL, about 0.7 ng/mL, about 0.8 ng/mL, about 0.9 ng/mL, about 1.0 ng/mL, about 2.0 ng/mL, about 3.0 ng/mL, about 4.0 ng/mL, about 5 ng/mL, or about 5.5 ng/mL of chymase in serum identify the subject as having or as having an increased risk of developing infectious disease associated with hemorrhaging and vascular leakage.

The reference level in this method can be the level of chymase in a patient with a severe form of infectious disease. Levels greater than or equal to about 5.0 ng/mL, about 5.5 ng/mL, about 5.6 ng/mL, about 5.7 ng/mL, about 5.8 ng/mL, about 5.9 ng/mL, about 6.0 ng/mL, about 6.1 ng/mL, about 6.2 ng/mL, about 6.3 ng/mL, about 6.4 ng/mL, about 6.5 ng/mL, about 7.0 ng/mL, about 8.0. ng/mL, about 9.0 ng/mL, about 10.0 ng/mL, about 11.0 ng/mL, or about 12.0 ng/mL of chymase in serum identify the subject as having or as having an increased risk of developing infectious disease associated with hemorrhaging and vascular leakage.

(a) Mild Form

The reference level in this method described above can be the level of chymase in a healthy patient. Levels greater than or equal to about 0.05 ng/mL, about 0.1 ng/mL, about 0.2 ng/mL, about 0.3 ng/mL, about 0.4 ng/mL, about 0.5 ng/mL, about 0.6 ng/mL, about 0.7 ng/mL, about 0.8 ng/mL, about 0.9 ng/mL, or about 1.0 ng/mL, of chymase in serum identify the subject as having or as having an increased risk of developing a mild form of infectious disease associated with hemorrhaging and vascular leakage.

The reference level in this method can be the level of chymase in a patient with a mild form of infectious disease. Levels greater than or equal to about 0.5 ng/mL, about 0.6 ng/mL, about 0.7 ng/mL, about 0.8 ng/mL, about 0.9 ng/mL, about 1.0 ng/mL, about 2.0 ng/mL, about 3.0 ng/mL, about 4.0 ng/mL, about 5 ng/mL, or about 5.5 ng/mL of chymase in serum identify the subject as having or as having an increased risk of developing a mild form of infectious disease associated with hemorrhaging and vascular leakage.

The reference level in this method can be the level of chymase in a patient with a severe form of infectious disease. Levels less than or equal to about 5.0 ng/mL, about 5.5 ng/mL, about 5.6 ng/mL, about 5.7 ng/mL, about 5.8 ng/mL, about 5.9 ng/mL, about 6.0 ng/mL, about 6.1 ng/mL, about 6.2 ng/mL, about 6.3 ng/mL, about 6.4 ng/mL, about 6.5 ng/mL, about 7.0 ng/mL, about 8.0. ng/mL, about 9.0 ng/mL, about 10.0 ng/mL, about 11.0 ng/mL, or about 12.0 ng/mL but greater than or equal to about 0.5 ng/mL, about 0.6 ng/mL, about 0.7 ng/mL, about 0.8 ng/mL, about 0.9 ng/mL, about 1.0 ng/mL, about 2.0 ng/mL, about 3.0 ng/mL, about 4.0 ng/mL, about 5 ng/mL, or about 5.5 ng/mL of chymase in serum identify the subject as having or as having an increased risk of developing a mild form of infectious disease associated with hemorrhaging and vascular leakage.

(b) Severe Form

The reference level in this method can be the level of chymase in a patient with a severe form of infectious disease. Levels greater than or equal to about 5.0 ng/mL, about 5.5 ng/mL, about 5.6 ng/mL, about 5.7 ng/mL, about 5.8 ng/mL, about 5.9 ng/mL, about 6.0 ng/mL, about 6.1 ng/mL, about 6.2 ng/mL, about 6.3 ng/mL, about 6.4 ng/mL, about 6.5 ng/mL, about 7.0 ng/mL, about 8.0. ng/mL, about 9.0 ng/mL, about 10.0 ng/mL, about 11.0 ng/mL, or about 12.0 ng/mL of chymase in serum identify the subject as having or as having an increased risk of developing a severe form of infectious disease associated with hemorrhaging and vascular leakage.

(3) Ranges of Reference Levels

The reference level in this method can be the level of chymase in a healthy patient. Levels of chymase in serum that are greater than about 1-fold, about 2-fold, about 3-fold, about 4-fold, about 5-fold, about 6-fold, about 7-fold, about 8-fold, about 9-fold, about 10-fold, about 15-fold, about 20-fold, about 25-fold, about 30-fold, about 35-fold, or about 40-fold, compared to the reference level of chymase identify the subject as having or as having an increased risk of developing infectious disease associated with hemorrhaging and vascular leakage.

The reference level in this method can be the level of chymase in a healthy patient. Levels of chymase in serum that are greater than about 1-fold, about 2-fold, about 3-fold, about 4-fold, about 5-fold, about 6-fold, about 7-fold, about 8-fold, about 9-fold, about 10-fold, about 15-fold, about 20-fold, about 25-fold, about 30-fold, about 35-fold, or about 40-fold, compared to the reference level of chymase identify the subject as having or as having an increased risk of developing a mild or severe form of infectious disease associated with hemorrhaging and vascular leakage.

The reference level in this method can be the level of chymase in a patient with a severe form of the infectious disease. Levels of chymase in serum that are greater than about 1-fold, about 2-fold, about 3-fold, about 4-fold, about 5-fold, about 6-fold, about 7-fold, about 8-fold, about 9-fold, about 10-fold, about 15-fold, about 20-fold, about 25-fold, about 30-fold, about 35-fold, or about 40-fold, compared to the reference level of chymase identify the subject as having or as having an increased risk of developing a severe form of infectious disease associated with hemorrhaging and vascular leakage.

13. TREATMENT

The subject identified in the method described above as having infectious disease is treated with an infectious disease treatment regimen.

a. Infectious Disease Treatment Regimen

The subject identified in the methods described above having levels of at least one biomarker less than, greater than or equal to the values discussed above is identified as a patient having or at risk of having an infectious disease that involves hemorrhaging or pathological vascular leakage. The subject is then treated for the infectious disease. Treatment of the infectious disease may include administering a mast cell modulator as described above and/or treating the symptoms of infectious disease, such as administering painkillers, fluid replacement, fever reduction medicines, antiviral drugs, such as Ribavirin, convalescent-phase plasma therapy, and vaccines.

b. Aggressive Treatment Regimen

The subject identified in the methods described above having levels of at least one biomarker greater than or equal to values discussed above is identified as a patient having or at risk of having a severe form of the infectious disease. The subject is then treated with a more aggressive therapy. Aggressive Treatment of the severe form of the infectious disease may include administering an infectious disease treatment regimen, as described above, and/or a transfusion of fresh blood or platelets to correct bleeding problems, intravenous (IV) fluids and electrolytes to correct electrolyte imbalances, oxygen therapy to treat abnormally low blood oxygen, and rehydration with intravenous (IV) fluids to treat dehydration.

c. Timing of the Treatment

The treatment regimen may be administered to the subject before onset of infection, at onset of infection, after onset of infection; before vascular leakage, at onset of vascular leakage, after onset of vascular leakage.

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

14. EXAMPLES

The present invention has multiple aspects, illustrated by the following non-limiting examples.

Example 1

Assessment of Contribution of MCs to DENV-Induced Vasculopathy

Figure 1:
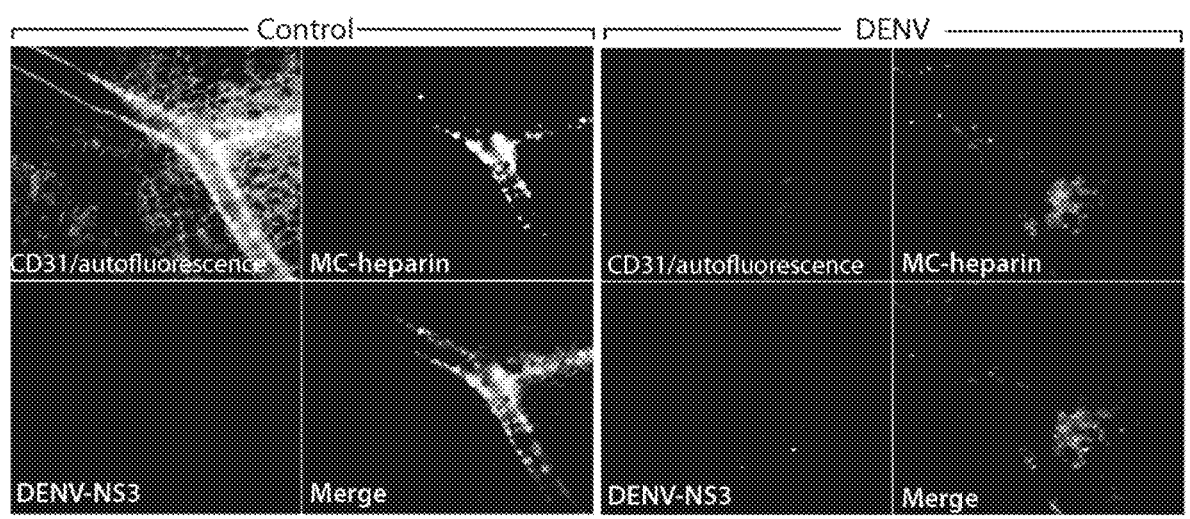
FIG. 1 shows images of control (left) and DENV-infected mesentery tissue (right) in channel series showing staining for blood vessels (CD31/autofluorescence), MC granules (MC-heparin by probing for Avidin), and viral replication (DENV-NS3), as well as the merged image (Merge).
Figure 2A:
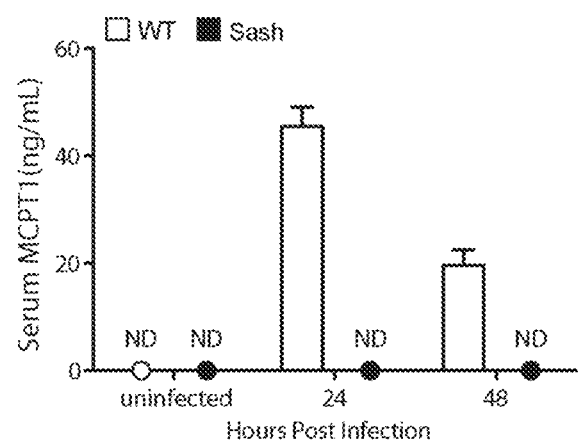
FIGS. 2A-2C show graphs showing serum concentration of MCPT1 in WT or Sash mice (mice that lack mast cells due to genetic deficiency) and that DENV-induced vascular leakage is MC-dependent.
Figure 2B:
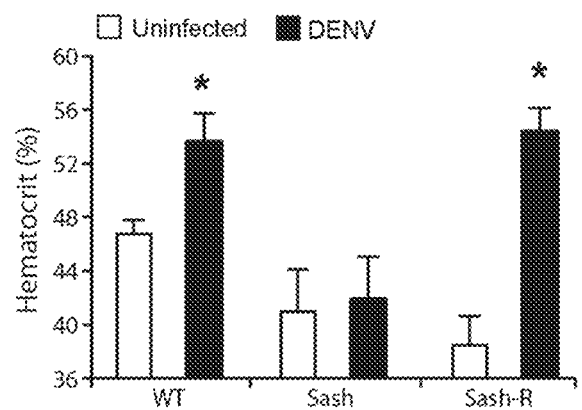
Figure 3:
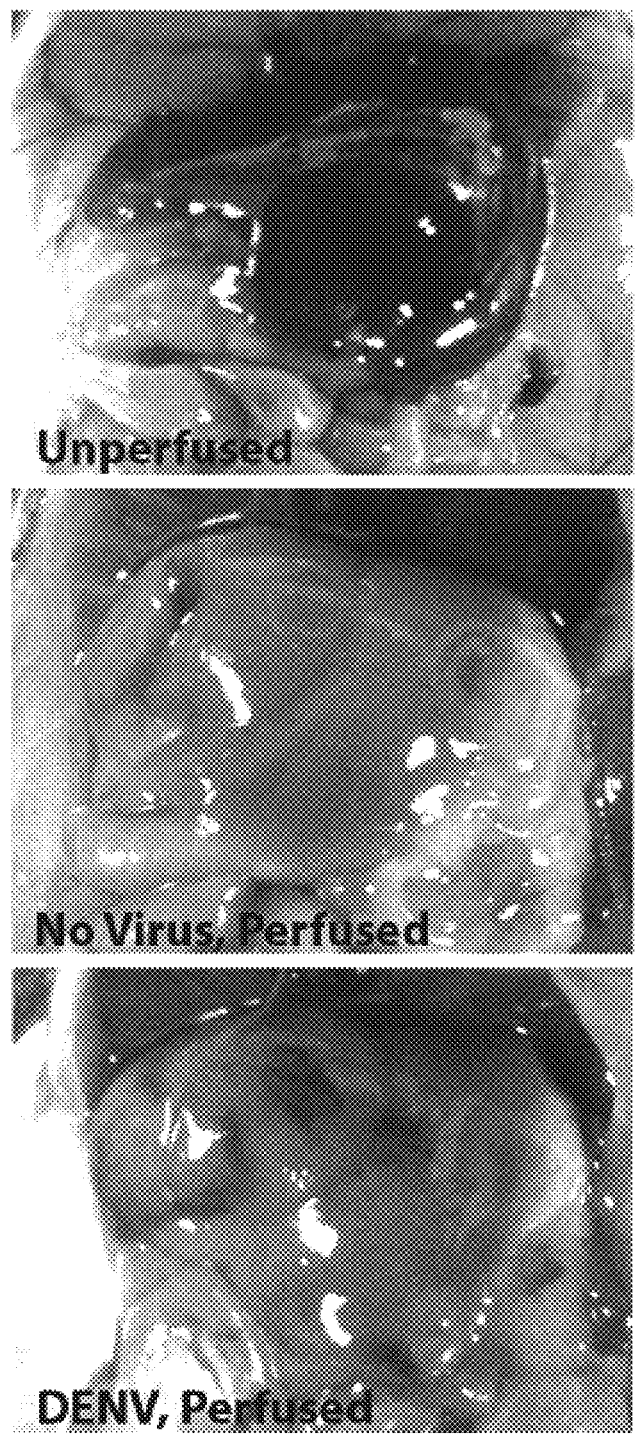
FIG. 3 shows images from WT mouse model to study DENV-induced vascular leakage. Uninfected mice, or mice infected with $1 \times 10^6$ pfu of DENV were injected with 100 µL of 5% Evans Blue dye 30 minutes prior to euthanasia. The top panel shows that livers appeared normal during necropsy. The middle panel shows perfusion of mice with saline eliminates blood in the vasculature. The bottom panel shows that in mice infected with DENV, vascular permeability can be visualized due to remaining blood and Evans Blue dye within tissues after saline perfusion, resulting in visible dark patches on organs. This contrast is particularly striking in the liver, a Dengue-target organ.

Support for the hypothesis that the role of MCs modulate the vascular endothelium during DENV infection with pathological consequences, images were taken showing that MC activation, DENV infection and loss of vascular structure appear intimately associated in infected tissues. The images in FIG. 1 indicate that DENV vasculopathy accompanies MC activation. Mesentery tissue from the DENV-permissive mouse strain, AG129, was isolated from control or DENV-infected tissue at 24 hr after i.p. injection to $2 \times 10^5$ pfu of DENV strain Eden2, followed by immunostaining in whole mount and viewing at 20× magnification. MCs can be observed lining the blood vessels in control tissue (left). Discrete avidin-staining particles suggest extensive degranulation in DENV-infected mesentery (right). Note that the endothelial junction marker, CD31, appears reduced and that NS3 staining is only present in the DENV-infected panel (right). L designates the lumen of the blood vessel in both panels To experimentally assess the contributions of MCs to DENV-induced vasculopathy, a mouse model was developed to compare the DENV-induced vascular leakage in immunologically intact hosts (WT) to mice lacking MCs (Sash). Development of a WT model was necessary in order to be able to assess the role of MCs within the context of a host that is able to generate normal immune responses, whether productive or pathological. To determine if DENV-infected WT mice can display systemic levels of MC activation, the MC-specific product, mast cell protease 1 (MCPT1), which is a chymase, was measured in mouse serum by ELISA. In WT mice, after i.p. injection of DENV, MCPT1 was detectable in the serum at 24 hr and continuing beyond 48 hr (see FIG. 2A). FIG. 2A shows that MCPT1 was not detected (ND) in uninfected WT mice and uninfected or infected Sash mice. Error bars represent the SEM of ELISA replicates using pooled serum samples. To compare vascular leakage in infected vs. uninfected WT or Sash mice. FIGS. 2A and 2B indicate that DENV-induced vascular leakage is MC-dependent As expected, Sash mice, which are MC-deficient model (see, e.g., Grimbaldestron, M. A. et al. (2005) Am. J. Pathol. 167:835-848), have undetectable serum levels of MCPT1 as baseline, as do uninfected congenic wild-type (WT) controls (FIG. 2A). To examine vascular leakage, mice infected with DENV were injected by tail vein with the tracking dye, Evans Blue, 30 minutes prior to euthanasia at a 24 hr time point. Initial examination of the internal organs of mice did not reveal visible leakage of the dye (FIG. 3), which is consistent with the observations by others that immunocompetent WT mice do not exhibit gross pathological vascular leakage with DENV infection (see, e.g., Raut, C. G. et al. (1996) Acta. Virol. 40:143-146).

This model was then used to determine both that MCs contribute to vascular leakage and that specific MC products are detectable in the sera of infected hosts.

Figure 4:
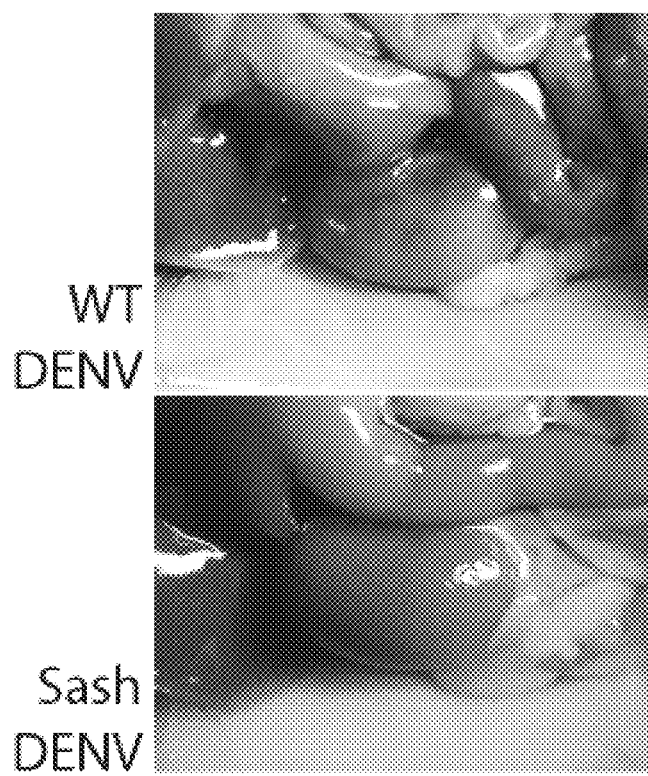
FIG. 4 shows images indicating MC-dependent DENV-induced vascular leakage in the kidney. WT mice (top panel) and Sash mice (bottom panel) were infected with $1 \times 10^6$ pfu of DENV. After 24 hours, mice were injected by tail vein with 100 µL of 5% Evans Blue dye, 30 minutes prior to euthanasia. In saline-perfused mice, vascular leakage was visible in the kidneys of WT but not Sash mice after DENV infection.

Using this Evans Blue perfusion model, the extent of vascular leakage induced in 24 hr after i.p. instillation of $1 \times 10^6$ plaque-forming units (pfu) of DENV in WT and Sash mice was determined. After perfusion, WT mice showed visually perceivable increases in vascular permeability in the liver that were supported by Evans Blue quantitation, however, Sash mice did not (FIG. 2B). FIG. 2B shows results of Evans blue quantitation in liver tissue. Images of mouse livers after perfusion are presented below the corresponding graph bars. Additional organs, such as the kidney, also showed evidence of MC-dependent leakage of blood into the tissues (FIG. 4A) that was not apparent in Sash mice (FIG. 4B).

Figure 2C:
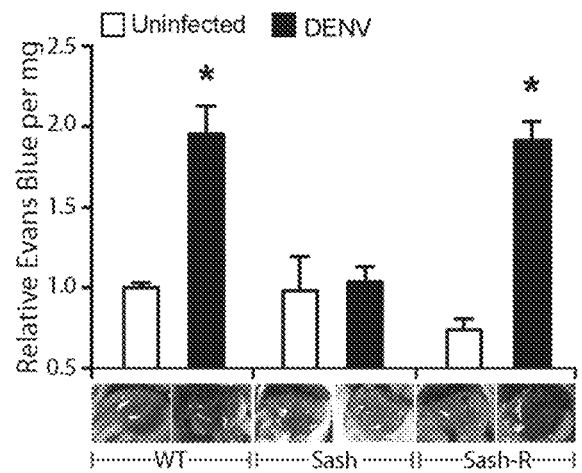

Sash mice that had been repleted intravenously with bone marrow-derived MCs (hereafter termed Sash-R mice) showed restored increased in vascular permeability with DENV challenge, determined by Evans Blue quantitation in tissues (FIG. 2B). Since the liver of mice contains very few MCs compared to other species such as humans, these findings suggested that systemic MC effects were likely responsible for the observed vascular changes (see, e.g., Koda, W. et al. (2000) Lab. Invest. 80:1007-1017; Bois, P. et al. (1964) Am. J. Physiol. 206:338-340). To support the observation of increased dye leakage, hematocrit analysis was also performed using blood samples from mice. This test is one that is used in some cases to diagnose DENV pathology clinically by measuring the packed red blood cell volume from the blood and, therefore, it is a measure of plasma loss (see, e.g., Special Programme for Research and Training in Tropical Diseases, WHO Dengue: guidelines for diagnosis, treatment, prevention, and control. (2009) New ed. Geneva:TDR:World Health Organization). The results of hematocrit analysis also supported the dye leakage studies presented herein, where MC-sufficient animals (both WT and Sash-R) had elevated hematocrit values with DENV infection, but Sash mice did not (FIG. 2C). FIG. 2C shows results of hematocrit analysis using blood obtained 24 hr after infection with DENV. For FIGS. 2B and 2C, error bars represent the SEM where values were obtained from individual infected mice n≥3. * indicates a significant increase over uninfected controls; $p \leq 0.05$. It was also found that MC-dependent vascular leakage directly correlated with increased MC-derived product MCPT1 (FIG. 2A). These findings cumulatively point to a pivotal role for MCs in promoting DENV-induced increased in vascular permeability.

Example 2

Therapeutic Targeting of MCs to Reduce Vascular Leakage During DENV Infection

Figure 5A:
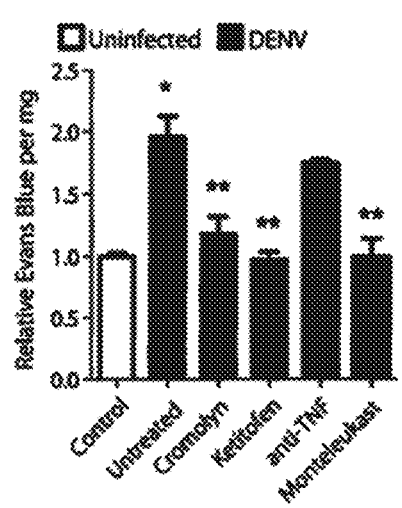
FIGS. 5A and 5B show graphs indicating that drugs targeting MCs and their products improve DENV-induced vasculopathy.

Due to the contributions of MCs to many pathological inflammatory disorders, there are a number of available drugs that target MCs or products that they produce after activation. Informed by the presented herein suggesting that MCs augment DENV-induced vascular leakage in mice (FIGS. 1-2), it was hypothesized that drugs known to stabilize MCs or block activity of key MC products could potentially be very effective in reducing vascular leakage during DENV infections. This hypothesis was tested by blocking DENV induced vascular leakage using a panel of such drugs. For the purposes of this study, two MC-stabilizing compounds that are clinically available were utilized: cromolyn and ketotifen, and two treatments that block MC products that are known to promote vascular leakage, an anti-TNF blocking antibody and montelukast, an inhibitor of leukotriene synthesis (see, e.g., Theoharides, T. C. et al. (1980) Science 207:80-82; McClean, S. P. et al. (1989) J. Allergy Clin Immunol. 83:738-741; and Busse, W. W. et al. (1999) Clin. Exp. Allergy 29 Suppl 2:110-115). None of these drugs act exclusively on MCs or MC-derived products but they are known to modulate the functions of MCs effectively in a clinical context. Drugs were administered once, 30 minutes after i.p. instillation of 1×106 DENV and vascular leakage assessed 1 day after infection. Both MC-stabilizing compounds significantly decreased vascular leakage compared to untreated DENV alone, as quantitated by Evans Blue leakage as well as hematocrit analysis (FIG. 5A).

Figure 5B:
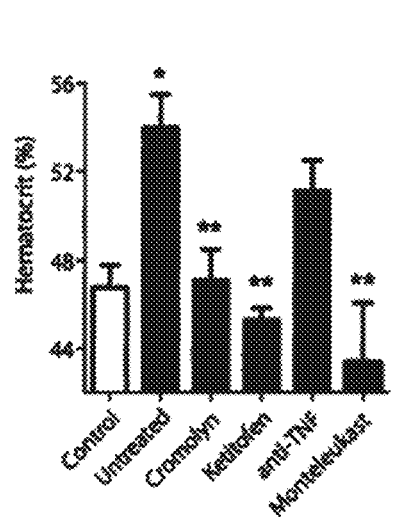

Blocking TNF has previously been shown to be effective in limiting vascular leakage at late time points of infection in immunocompromised mice lacking Type I and II interferon receptors (IFN-$\alpha,\beta,\gamma$-R$^{-/-}$), which is a mouse model of DENV viremia (see, e.g., Zellweger, R. M. et al. (2010) Cell Host Microbe. 7:128-139). In vitro, MC-derived TNF from DENV-exposed MCs has also been shown to promote adhesion molecule expression on co-cultured endothelial cells. In the WT mouse model presented here, when TNF-blocking antibodies were administered 1 hr after systemic infection was initiated by i.p. injection, the average Evans Blue dye leakage and hematocrit values were lower; however, this did not reach statistical significance (FIG. 5A). Blocking leukotriene function using the drug monteleukast also allowed striking, significant reductions in dye leakage compared to untreated mice (FIG. 5A), suggesting leukotrienes can also contribute to DENV-induced vascular permeability. Although cromolyn's inhibitory influence on MCs is well established, to support a direct effect of the MC-stabilization strategy on MCs in the present DENV infection model, serum MCPT1 was again compared in untreated and cromolyn-treated DENV-infected mice (see, e.g., Theoharides, T. C. et al. (1980) supra). As expected, levels of MCPT1 were reduced by cromolyn treatment at 24 hr, and by 48 hr, serum MCPT1 was undetectable in treated mice, yet still elevated in untreated mice (FIG. 5B). Three drugs from this panel, cromolyn, ketotifen, and monteleukast (also marketed as Singulair) were all successful in restoring both the levels of tissue dye detection and hematocrit values to levels that were not statistically different from baseline levels (FIG. 5A). These data highlight the potential of MCs to serve as therapeutic targets to limit DENV pathology.

Figure 5B:
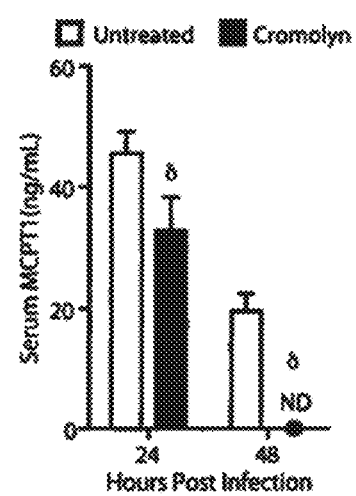

Additional formulations of MC targeting or stabilizing drugs may be effective individually or on combination, including but not restricted to the class of cromone compounds such as cromolyn, cromoglicate, nedocromil, pemirolast, loxoxamide, and others, frequently administered in various salt forms (e.g., sodium, potassium, chloride, hydrochloride, etc.). Additional MC stabilizers include ketotifin, rupatadine, olopatadine, tranilast, glucosamine, N-acetylglucosamine, FPL 52694, aloe vera, some flavonoids (e.g., quercetin), condroitinm sulfate, dehydroleucodine, and mast cell stabilizer RF002. Effective targeting of leukotrienes has been demonstrated herein (see FIG. 5), and additionally, more effective combinations for targeting of specific MC products may be employed including, but not limited to, additional leukotriene blockers (e.g., receptor agonists, including zafirlukast and monolukast, and synthesis inhibitors, such as Zileuton), histamine blockers or receptors agonists (e.g., loratadine, cetirizine, clemastine, fexofenadine, diphenhydramine, chlorpheniramine, azelastine, olopatadine, ketotifen, naphazoline, emedastine, ebrotidine, etc.), platelet activating factor (by blocking peptides/receptor agonists such as SM-12502 and rupatadine or PAF-targeting antibodies), tumor necrosis factor (immunomodulators such as infliximab, adalimumab, certolizumab pegol, golimumab, additional monoclonal antibodies, etanercept, xanthine derivatives, bupropion, curcumin, catechins, etc.) proteases (e.g., agents blocking mast cell proteases including tryptases and chymases), VEGF (including bevacizumab, ranibizumab, iapatinib, sunitinib sorafenib, axitinib, pazopanib, thiazolidinediones, etc.) and agents targeting additional mast cell derived cytokines. These drugs can be administered by various routes, including but not limited to orally, ocularly, nasally, intravenously, topically, as aerosols, suppository, etc. and may be used in combination. These drugs may also be given as a preventative treatment or therapeutically at any stage of disease progression, before or after vascular leakage symptoms, and the like. Therefore, disclosed herein are several candidate drugs that target MCs or their products that may be effective in limiting or preventing DENV pathology in a clinical setting and these drugs have been used in other contexts, although never shown to be effective in an infectious context (see, e.g., McFadden, E. R. et al. (1992) N. Engl. J. Med 327:1928-1937; Leff, J. A. et al. (1998) N. Eng. J. Med. 339:147-152). Furthermore, it has been noted that many viruses that cause hemorrhaging are not closely related evolutionarily but have developed a similar pathology in humans, raising the potential that a unique mechanism of immune pathology may exist due to the response of the human host to viruses (see, e.g., LeDuc, J. W. (1989) supra). The results presented herein suggest that MC stabilization during or prior to infection is likely to be an effective broad strategy to prevent or treat hemorrhagic complications of viremia or even, in certain cases, bacteremia.

Since DENV is quickly cleared from WT mice, an experiment using IFN-α,β,γ-R$^{-/-}$ mice was performed since these mice can sustain replicating DENV infection for many days (Zellweger, R. M. et al. (2010) supra). This model allowed for the delay or treatment with cromolyn until 1 day after systemic infection was initiated via intra-peritoneal injection, as was performed previously using the DENV clinical isolate, Eden2, and this allowed a time course of infection that is more analogous to the human disease (Halstead, S. B. (2007), supra). When blood was collected 3 days after infection and after 2 daily doses of cromolyn, it was observed that hematocrit values reduced significantly compared to DENV-infected, untreated mice (FIG. 6).

Although there is considerable disagreement in the Dengue field, some groups have also reported the ability to enhance the severity of Dengue infection with serum of post-immune animals (Halstead, S. B. (2007), supra). This data is thought to support the observations by some groups that a secondary exposure to DENV is more likely to promote severe complications in human patients than a primary exposure. Based in this hypothesis that secondary exposure to DENV is potentially more severe due to the presence of pre-existing antibodies, an experiment was undertaken to determine if the MC stabilization strategy can be effective in a model of secondary infection, where antibodies against DENV are perfused into mice prior to infection. In this context, like primary infection, MC stabilization with the drug cromolyn improved vascular integrity significantly (FIG. 6). In sum, these data suggest that drugs that stabilize MCs or block the activity of various key MC products can markedly reduce DENV induced vascular leakage and severity of infection.

Example 3

Use of a MC Product as a Biomarker for the Diagnosis of Severe DENV Infections

The experiments described herein revealed that MCs contributed significantly to vascular leakage and further, that there appeared to be a correlation between severity of vascular leakage and detection of MCPT1 in the sera of DENV infected mice (FIG. 2A). The human homologue of mouse MCPT1, chymase, is also a MC-derived product, known to increase vascular leakage over a prolonged time course (He, S. et al. (1998) Eur. J. Pharmacol. 352:91-98). Based on this, it was hypothesized that chymase might be a biomarker of DENV infection in humans and that it might be possible to predict the severity of DENV outcomes by monitoring MC proteases, such as chymase, in the sera of DENV-infected patients. To validate this hypothesis, chymase levels were assessed by ELISA in human DENV patients (FIG. 7A).

All sera were obtained from a previously described DENV clinical study (see, e.g., Low, J. G. et al. (2006) Ann Acad Med Singapore 35:783-789 and Fink, J. et al. (2007) PLos Negl Trop Dis 1:e86), where early serum samples were obtained during acute DENV infection (1-3 days after onset of fever), followed by a second sample during the defervescent stage of infection (4-7 days after onset of fever). The sera tested fell into the following groups: (1) control healthy human sera; (2) control sera from individuals with fever that were referred to the study as possible DENV cases but were negative for DENV by laboratory tests; (3) sera from patients that were positive for DF by clinical diagnosis as well as RT-PCR; and (4) sera from patients that were DENV positive by clinical diagnosis, molecular tests, and were also diagnosed during the study to have DHF, rather than the less severe DF. Strikingly, it was found that those patients that were diagnosed with DF or DHF showed chymase levels in serum obtained during the acute phase of infection were significantly higher than levels in the serum of either healthy controls or individuals with fever that were not confirmed to be DENV positive laboratory tests (FIG. 7A). During the acute phase of infection, DF patients displayed an approximate 10-fold increase in serum chymase compared to healthy individuals of DENV-negative patients while, in DHF patients, a 30-fold increase in chymase was detected (FIG. 7B). Since this amounts to an approximate 3-fold increase in the levels of serum chymase in the blood of DHF patients compared to DF patients, this finding also illustrates a correlation between the levels of chymase and the severity of vasculopathy experienced in DENV-infected humans (FIG. 7B). This trend, where chymase levels were correlated with DENV severity, persisted to the second time point of blood collection (FIG. 7B), illustrating a prolonged course of elevated MC products occurs during infection. Human DENV-infection follows a disease course where acute infection is characterized by high viremia and fever, followed by either resolution of hemorrhagic complications that usually occur during the defervescent phase (Halstead, S. B. (2007), supra). These opposing outcomes are difficult to predict early in infection. These results suggest the MC chymase is a highly effective biomarker for the prediction of severe DENV disease outcomes. For this clinical study, there was not a single "false-negative" DHF patient with chymase levels at control values, or a single "false-negative" in the control or febrile non-DENV groups with detected chymase levels elevated to the range of DHF levels.

The data presented herein provides a basis for using MC products to identify individuals at highest risk for hemorrhagic complications and suggests the development of a diagnostic test to predict the probability of severe complications. This detection method also lends itself to rapid detection techniques. A test as one described herein could rely on basic protein chemistry to identify a unique protein profile that is highly predictive of Dengue infection. The protein profile of the prototype test could include the MC-derived product human chymase and a virus protein, such as NS1, although additional MC and DENV-derived products with effects on the vasculature include tryptase, leukotrienes, TNF, VEGF, histamine and others (see, e.g., Kunder, C. A. et al. (2011) Blood 118:5383-5393). Dengue has 10 proteins, which could be used in combination with MC products to concurrently predict infection and severity. As an extension, tests could be used or identifying the severity of hemorrhaging concurrently with the virus or virus strain by combining the antigens from multiple viruses onto a single test. In applications such as for travelers or military personnel, this would facilitate appropriate diagnosis and medical care for an individual.

Example 4

MC products directly promote the permeability of vascular endothelial cells. This permeability can be blocked with MC-targeting drugs (FIG. 8): (a) Trans-well assays demonstrate the direct activity of MCs and MC products on permeability of a monolayer of endothelial (EOMA) cells. Supernatants were collected from 1×105 bone marrow derived mast cells (BMMCs), either untreated or activated with DENV (MOI 1), after a 1 hr incubation and these supernatants or virus containing media control were exposed to EOMA cells grown on trans-wells (n=3). Trans-endothelial resistance (TER) was measured using an Ohm meter prior to treatment and at 24 hr after treatment to determine the relative change in resistance. For treatment with either monteleukast or a cocktail of chymase inhibitors, the drugs were added to the trans-well insert just prior to treatment with MC supernatants. For cromolyn inhibition of BMMCs, cromolyn was incubated with MCs during their exposure to DENV. Significance was determined by ANOVA. δ indicates a significant decrease in TER compared to exposure to supernatants from untreated MC or DENV alone treatment ($p<0.05$). Groups treated with monteleukast or chymase inhibitor cocktail significantly increased TER over untreated EOMA cells exposed to supernatant from DENV activated MCs; *$p<0.05$. Cromolyn treatment during DENV exposure resulted in increased TER over supernatants from untreated DENV-exposed BMMCs **$p<0.01$. (b) To demonstrate the contributions of individual MC products to endothelial monolayer permeability, trans well assays were performed using peritoneal and pleural cavity MCs isolated by antibody labeling and magnetic separation. Purified MCs, which have abundant eosinophilic cytoplasmic granules, are imaged in the inset. Purified MCs from WT, 5-LO-KO, or TNF-KO mice were untreated or treated with DENV (MOI=5) for 1 hr prior to isolation of supernatant for exposure to EOMA cells (left) or a second independent vascular endothelial cell line, SVEC4-10EHR1 (right). Supernatants from both WT and TNF-KO MCs resulted in a significant reduction in the TER of EOMA cells with exposure compared to controls, determined by ANOVA; for δ $p<0.05$. 5-LO-KO showed a trend towards slightly reduced TER, but this was not significant since $p=0.06$. DENV activated WT MCs promoted significantly reduced relative TER readings compared to DENV activated 5-LO-KO MCs, determined by T test *$p=0.01$.

Example 5

Dengue-activated human mast cells also promote permeability of human vascular endothelial cells in vitro. This can be blocked to varying extents with MC-targeting drugs. (FIG. 9). Trans-well assays demonstrate the direct activity of a products released by a human MC line treated by dengue virus on permeability of a monolayer of human endothelial (HUVEC) cells. Supernatants collected from MCs activated with DENV (MOI 1), after a 1 hr incubation or media alone, or virus-containing media control were exposed to HUVEC cells grown on trans-wells (n=3). Trans-endothelial resistance (TER, left panel) was measured using an Ohm meter prior to treatment and at 24 hr after treatment to determine the relative change in resistance. Drugs were applied to MCs or to HUVEC cells, as appropriate to attempt to block vascular permeability. After obtaining TER values, FITC dextran, a large dye impermeable to tight monolayers, was added to one side of the transwell insert. At 48 hr, the supernatant on the opposite side of the insert was sampled and the amount of FITC to measure the diffusion of large molecules. Consistent with the TER data, supernatant from DENV activated MCs allows the flow of dye across endothelial monolayers. This increased permeability can be blocked with some MC-targeting drugs, particularly those of the class of MC-stabilizers.

Example 6

Chymase is a Biomarker of Dengue Infection

Chymase was measured by ELISA in mouse serum over a 5-day time course after infection of with dengue virus (n=3-5 animals per day). As shown in FIG. 10, chymase levels were elevated beginning within 24 hours of infection and, therefore, chymase is an early biomarker of dengue infection.

Example 7

Additional Mast Cell Products are Biomarkers of Dengue Infection

FIG. 11 shows that in addition to chymase, cytokines and vasoactive factors produced by mast cells, such as IL-6 (FIG. 11A) and VEGF (FIG. 11B) are markers of dengue infection in mice. Other cytokines including IFN-gamma (FIG. 11C) and TNF (FIG. 11D) were elevated in only some animals, and therefore were not consistently biomarkers of dengue infection. Lipid-based products that are abundantly produced by mast cells, such as cysteinyl leukotrienes (CystLT) (FIG. 11E) and prostaglandins (PG) (FIG. 11F) were also significantly increased in the serum of dengue-infected mice over controls. For all panels, * designates $p>0.05$, determined by Student's unpaired T test. Concentrations of inflammatory or vasoactive products were determined by ELISA using un-pooled mouse serum obtained 24 hours after infection with dengue virus by intra-peritoneal infection. For each panel, n=3 mice.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of inhibiting vascular leakage in a subject having a Japanese encephalitis virus (JEV) infection, the method comprising:
    (a) obtaining a biological sample from the subject;
    (b) determining the level of chymase, tryptase, or a combination thereof in the biological sample from the subject;
    (c) comparing the level of chymase, tryptase, or a combination thereof in the biological sample to a reference level of chymase, tryptase, or a combination thereof;
    (d) identifying the subject as having a JEV infection if the level of chymase, tryptase, or a combination thereof is greater than the reference level of chymase, tryptase, or a combination thereof; and
    (e) administering a mast cell modulator to the subject identified as having a JEV infection, wherein the mast cell modulator comprises cromolym, ketifen, or montelukast.

2. The method of claim 1, wherein the reference level of chymase, tryptase, or a combination thereof is the level of chymase, tryptase, or a combination thereof in a control sample from a healthy patient.

3. The method of claim 2, wherein the reference level is about 0.18 ng/mL to about 0.5 ng/mL.

4. The method of claim 1, wherein the reference level 9f chymase, tryptase, or a combination thereof is the level of chymase, tryptase, or a combination thereof in a control sample from a patient having a mild form of JEV infection.

5. The method of claim 1, wherein the reference level is about 0.8 ng/mL to about 6.0 ng/mL.

6. The method of claim 1, wherein the reference level of chymase, tryptase, or a combination thereof is the level of chymase, tryptase, or a combination thereof in a control sample from a patient having a severe form of JEV infection.

7. The method of claim 6, wherein the reference level is greater than about 6.0 ng/mL.

8. The method of claim 2, wherein the level of chymase, tryptase, or a combination thereof in the biological sample is at least two times greater than the level of chymase, tryptase, or a combination thereof in the control sample.

9. A method of inhibiting vascular leakage in a subject having a mild or severe form of Japanese encephalitis virus (JEV) infection, the method comprising:
    (a) obtaining a biological sample from the subject;
    (b) determining the level of chymase, tryptase, or a combination thereof in the biological sample from the subject;
    (c) comparing the level of chymase, tryptase, or a combination thereof in the biological sample to a first reference level of chymase, tryptase, or a combination thereof and a second reference level of chymase, tryptase, or a combination thereof;
    (d) correlating the level of chymase, tryptase, or a combination thereof in the biological sample with the mild or severe form of JEV infection in the subject, wherein if the level of chymase, tryptase, or a combination thereof is greater than the first reference level and the second reference level, the subject is diagnosed as having the severe form of JEV infection, and wherein if the level of chymase, tryptase, or a combination thereof is greater than the first reference level but less than the second reference level, the subject is diagnosed as having the mild form of JEV infection; and
    (e) administering a mast cell modulator with an aggressive treatment regimen to the subject identified as having the severe form of JEV infection or administering a mast cell modulator to the subject identified as having the mild form of JEV infection, wherein the mast cell modulator comprises cromolym, ketifen, or montelukast.

10. The method of claim 9, wherein the first reference level is the level of chymase, tryptase, or a combination thereof in a first control sample and the second reference level is the level of chymase, tryptase, or a combination thereof in a second control sample.

11. The method of claim 1, wherein the biological sample of a subject is selected from the group consisting of tissue sample, bodily fluid, whole blood, plasma, serum, urine, bronchoalveolar lavage fluid, saliva, tissue biopsy, and a cell culture suspension or fraction thereof.

12. The method of claim 1, wherein the mast cell modulator comprises montelukast.

13. The method of claim 9, wherein the aggressive treatment regimen comprises transfusing fresh blood or platelets, administering intravenous fluids, administering intravenous fluids and electrolytes, or administering oxygen therapy.

* * * * *